United States Patent [19]

Berg

[11] Patent Number: 5,047,023
[45] Date of Patent: Sep. 10, 1991

[54] ABSORBENT MEMBERS HAVING LOW DENSITY AND BASIS WEIGHT ACQUISITION ZONES

[75] Inventor: Charles J. Berg, Springfield Township, Hamilton County, Ohio

[73] Assignee: The Procter & Gamble Company, Cincinnati, Ohio

[21] Appl. No.: 656,101

[22] Filed: Feb. 11, 1991

Related U.S. Application Data

[63] Continuation of Ser. No. 512,626, Apr. 11, 1990, abandoned, which is a continuation of Ser. No. 147,375, Jan. 22, 1988, abandoned, which is a continuation-in-part of Ser. No. 887,584, Jul. 18, 1986, Pat. No. 4,834,735.

[51] Int. Cl.$^5$ ............................................. A61F 13/15
[52] U.S. Cl. ..................................... 604/368; 604/378
[58] Field of Search ............... 604/358, 364, 365, 367, 604/368, 371, 372, 374, 378–382, 385.1, 385.2

[56] References Cited

U.S. PATENT DOCUMENTS

| | | |
|---|---|---|
| Re. 29,789 | 10/1978 | Kolbach . |
| 3,017,304 | 1/1962 | Burgeni . |
| 3,371,667 | 3/1968 | Morse . |
| 3,403,681 | 10/1968 | Hoey et al. . |
| 3,441,023 | 4/1969 | Rijssenbeek . |
| 3,545,441 | 12/1970 | Gravdahl . |
| 3,592,194 | 7/1971 | Duncan . |
| 3,670,731 | 6/1972 | Harmon . |
| 3,766,922 | 10/1973 | Krusko . |
| 3,860,002 | 1/1975 | Kolbach . |
| 3,897,784 | 8/1975 | Fitzgerald . |
| 3,901,236 | 8/1975 | Assarsson et al. . |
| 3,908,659 | 9/1975 | Wehrmeyer et al. . |
| 3,927,673 | 12/1975 | Taylor . |
| 3,965,904 | 6/1976 | Mesek et al. . |
| 3,971,373 | 7/1976 | Braun . |
| 4,027,672 | 6/1977 | Karami . |
| 4,102,340 | 7/1978 | Mesek et al. . |
| 4,103,058 | 7/1978 | Humlicek . |
| 4,105,033 | 8/1978 | Chatterjee et al. . |
| 4,145,464 | 3/1979 | McConnell et al. . |
| 4,213,459 | 7/1980 | Sigl et al. . |
| 4,217,901 | 8/1980 | Bradstreet et al. . |
| 4,232,674 | 11/1980 | Melican . |

(List continued on next page.)

FOREIGN PATENT DOCUMENTS

| | | |
|---|---|---|
| 1128704 | 8/1982 | Canada . |
| 0062495 | 10/1982 | European Pat. Off. . |
| 156649 | 10/1985 | European Pat. Off. . |
| 0158914 | 10/1985 | European Pat. Off. . |
| 198683 | 10/1986 | European Pat. Off. . |
| 216147 | 4/1987 | European Pat. Off. . |
| 157788 | 12/1979 | Japan . |
| 65630 | 6/1981 | Japan . |
| 57-104 | 1/1982 | Japan . |
| 62463 | 3/1986 | Japan . |
| 106151 | 5/1986 | Japan . |
| 1500559 | 2/1978 | United Kingdom . |
| 2113731 | 8/1983 | United Kingdom . |
| 2124907 | 2/1984 | United Kingdom . |

OTHER PUBLICATIONS

Sanyo Chem. Ind. "Superabsorbent Polymer—SANWET IM-300/SANWET IM-1000"(1982).
Nippon Shokubai Kaguku Kogyo K.K., "Aqualic CA".
Stockhausen Inc.; "Favor SAB-901"; Jul. 1983.
BASF AG, "Luquasorb HC 9/80—Superabsorbent Based on Polyacrylic Acid for Aqueous Fluids".

Primary Examiner—Randall L. Green
Assistant Examiner—K. Reichle
Attorney, Agent, or Firm—Steven W. Miller; Richard C Witte

[57] ABSTRACT

An absorbent article wherein the deposition region of its absorbent member comprises a storage zone and an acquisition zone having a lower average density and a lower average basis weight per unit area than the storage area. The acquisition zone is positioned toward the front of either the absorbent member or the absorbent article so that the acquisition zone may most effectively and efficiently rapidly acquire discharged liquids. The absorbent member comprises a mixture of hydrophilic fibrous material and discrete particles of absorbent gelling material having a particular size distribution so as to enhance the absorbent capacity and acquisition rate of the absorbent member. The particles of absorbent gelling material are selected to have a mass median particle size greater than or equal to about 400 microns with the amounts of very large and very small particles preferably kept below certain minimum concentrations.

26 Claims, 5 Drawing Sheets

U.S. PATENT DOCUMENTS

| | | |
|---|---|---|
| 4,259,387 | 3/1981 | Mesek . |
| 4,276,338 | 6/1981 | Ludwa et al. . |
| 4,285,342 | 8/1981 | Mesek . |
| 4,333,463 | 6/1982 | Holtman . |
| 4,340,556 | 7/1982 | Ciencewicki . |
| 4,373,519 | 2/1983 | Errede et al. . |
| 4,381,782 | 5/1983 | Mazurak et al. . |
| 4,389,513 | 6/1983 | Miyazaki . |
| 4,397,644 | 8/1983 | Matthews et al. . |
| 4,401,795 | 8/1983 | Herman et al. . |
| 4,429,001 | 1/1984 | Kolpin et al. . |
| 4,443,512 | 4/1984 | Delvaux . |
| 4,449,979 | 5/1984 | Holtman . |
| 4,460,642 | 7/1984 | Errede et al. . |
| 4,496,358 | 1/1985 | Karami et al. . |
| 4,535,098 | 8/1985 | Evani et al. . |
| 4,551,199 | 11/1985 | Kock et al. . |
| 4,552,938 | 11/1985 | Makita et al. . |
| 4,559,050 | 12/1985 | Iskra . |
| 4,560,372 | 12/1985 | Pieniak . |
| 4,578,068 | 3/1986 | Kramer et al. . |
| 4,585,448 | 4/1986 | Enloe . |
| 4,587,308 | 5/1986 | Makita et al. . |
| 4,604,313 | 8/1986 | McFarland et al. . |
| 4,610,678 | 9/1986 | Weisman et al. . |
| 4,625,001 | 11/1986 | Tsubakimoto et al. . |
| 4,645,789 | 2/1987 | Dabi . |
| 4,654,039 | 3/1987 | Brandt et al. . |
| 4,655,757 | 8/1987 | McFarland et al. . |
| 4,657,537 | 4/1987 | Zimmerer . |
| 4,666,975 | 5/1987 | Yamasaki et al. . |
| 4,666,983 | 5/1987 | Tsubakimoto et al. . |
| 4,673,402 | 6/1987 | Weisman et al. . |
| 4,685,909 | 8/1987 | Berg et al. . |
| 4,685,915 | 8/1987 | Hasse et al. . |
| 4,699,619 | 10/1987 | Bernardin ............................ 604/368 |
| 4,699,823 | 10/1987 | Kellenberger et al. . |
| 4,834,735 | 5/1989 | Alemany et al. . |

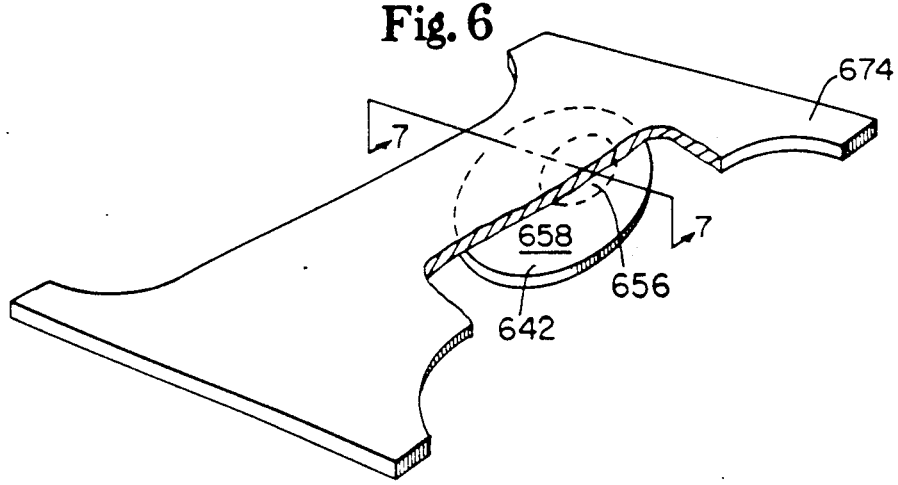
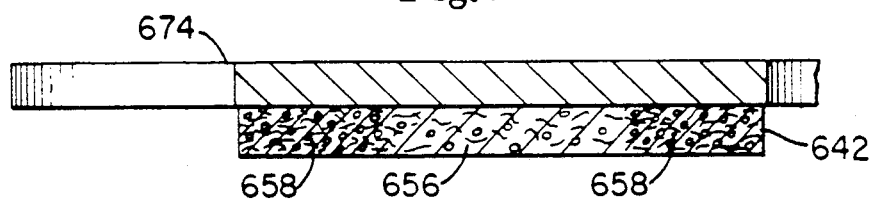
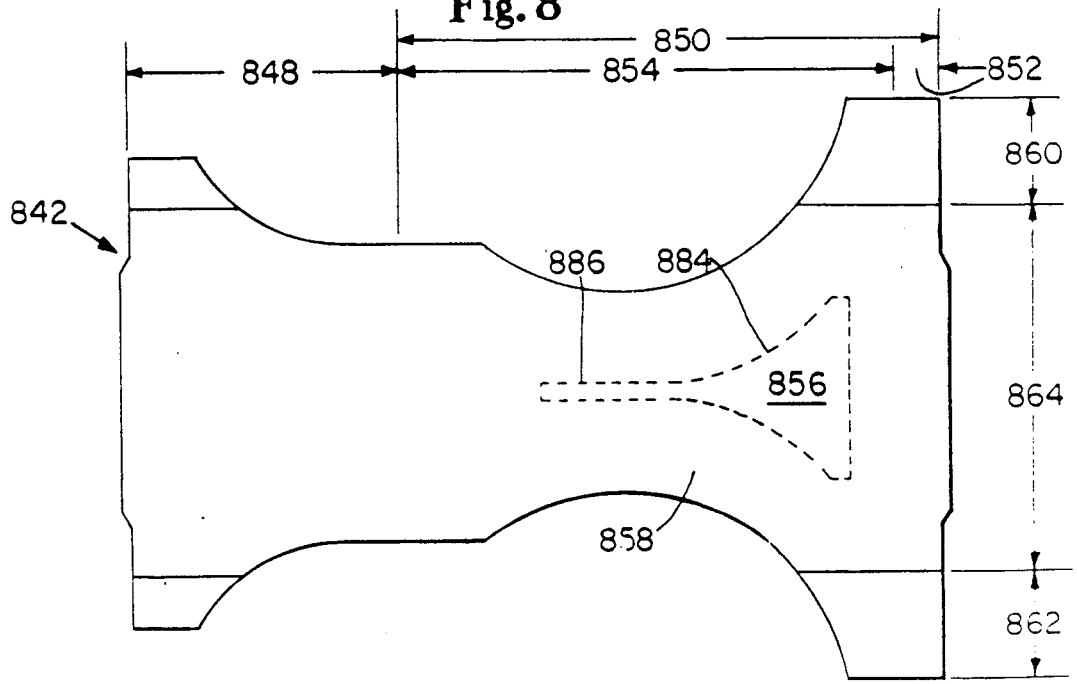

ABSORBENT MEMBERS HAVING LOW DENSITY AND BASIS WEIGHT ACQUISITION ZONES

This is a continuation of application Ser. No. 07/512,626, filed on Apr. 11, 1990, abandoned, which is a continuation of application Ser. No. 07/147,375, filed on Jan. 22, 1988, abandoned which is a continuation-in-part of application Ser. No. 887,584, filed on Jul. 18, 1986, now U.S. Pat. No. 4,834,735.

FIELD OF THE INVENTION

This invention relates to absorbent members (fibrous web structures) having a mixture of hydrophilic fibrous material and discrete particles of absorbent gelling material. More particularly, the invention relates to a relatively high density absorbent member having a relatively lower average density and lower average basis weight acquisition zone positioned in the area of typical liquid deposition to more quickly acquire and distribute liquids within the absorbent member.

BACKGROUND OF THE INVENTION

Absorbent articles such as disposable diapers, adult incontinent pads, sanitary napkins and the like are generally provided with absorbent members, fibrous web structures which comprise entangled masses of fibers, to receive and retain body liquids. In order for such absorbent articles to function efficiently, the absorbent members must quickly acquire body liquids into the structure from the point of application and subsequently distribute the body liquids within and throughout the absorbent member to provide maximum liquid containment. In addition, the absorbent members should be capable of retaining liquids when placed under loads. Prior art attempts to improve the effectiveness of such absorbent members have included distributing particles of absorbent gelling material throughout or in portions of the absorbent member. For example, U.S. Pat. No. 4,610,678, entitled "High-Density Absorbent Structures" which issued to Paul T. Weisman and Stephen A. Goldman on Sept. 9, 1986, discloses absorbent members wherein particles of absorbent gelling material (hydrogel) are dispersed in an air-laid web of hydrophilic fibrous material and compressed to a particular density. In addition, U.S. Pat. No. 4,673,402, entitled "Absorbent Articles With Dual-Layered Cores" which issued to Paul T. Weisman, Dawn I. Houghton and Dale A. Gellert on Jun. 16, 1987, discloses a dual-layer absorbent core wherein an absorbent acquisition layer overlays a lower fluid storage layer that consists essentially of a uniform combination of hydrophilic fibrous material and discrete particles of absorbent gelling material.

Absorbent gelling materials are polymeric materials which are capable of absorbing large quantities of liquids such as water and body wastes relative to their weight, and which are further capable of retaining such absorbed liquids under moderate pressures. These absorption characteristics of absorbent gelling materials make them especially useful for incorporation into absorbent articles such as disposable diapers, adult incontinent pads, sanitary napkins and the like. However, in spite of the extremely high absorption capacities of such absorbent gelling materials, their performance when used in disposable absorbent articles has still not been optimized.

The effectiveness of absorbent gelling materials in disposable absorbent articles is quite dependent upon the form, position, size, and/or manner in which the particles of absorbent gelling material are incorporated into the absorbent member. In some cases, for example, the effectiveness of absorbent members containing particles of absorbent gelling material can be adversely affected by a phenomenon called gel blocking. The term "gel blocking" describes a situation that occurs when a particle of absorbent gelling material is wetted, the surface of the particles swelling so as to inhibit liquid transmission into the interior of the absorbent member. Wetting of the interior of the absorbent member, therefore, takes place via a very slow diffusion process. In practical terms, this means that acquisition of liquids by the absorbent member is much slower than the discharge of the liquid to be absorbed, and leakage from the absorbent article may take place well before the particles of absorbent gelling material in the absorbent member are fully saturated or before the liquid can diffuse or wick past the "blocking" particles into the rest of the absorbent member. The slow acquisition rate also fails to take advantage of the rapid wicking of liquids to other parts of the absorbent member provided by a densified absorbent member containing particles of absorbent gelling material.

Thus, it would be advantageous to provide an absorbent member that more quickly acquires and distributes liquids within itself while minimizing gel blocking during the liquid acquisition phase. It is therefore a primary objective of the present invention to provide improved absorbent members which are especially effective and efficient in their use of absorbent gelling materials.

It is a further object of the present invention to provide absorbent members of improved capacity and efficiency by control of the particle size distribution of the absorbent gelling materials employed in the absorbent members.

SUMMARY OF THE INVENTION

The present invention provides absorbent articles such as disposable diapers, incontinent pads, sanitary napkins or the like that have absorbent members that is suitable for acquiring and containing liquids in an especially effective and efficient manner. Such absorbent articles comprise a liquid pervious topsheet, a liquid impervious backsheet, and an absorbent member positioned between the topsheet and the backsheet.

The absorbent member has a deposition region which comprises a storage zone of a relatively high density and high basis weight to absorb and retain liquids acquired by the absorbent member and an acquisition zone of a relatively lower average density and lower average basis weight than the storage zone to quickly acquire and temporarily hold discharged liquids. The absorbent member also comprises a mixture of hydrophilic fibrous material and discrete particles of absorbent gelling material.

In accordance with one aspect of the present invention, the acquisition zone is positioned toward the front of the absorbent member so that the acquisition zone may be positioned in the area of typical liquid deposition. The acquisition zone is also sized so that the top surface area of the acquisition zone comprises less than about 50% of the top surface area of the front section of the absorbent member.

In accordance with another aspect of the present invention, particles of absorbent gelling material having a particle size distribution such that the particles have a mass median particle size greater than or equal to about 400 microns is mixed with hydrophilic fibrous material to minimize gel blocking and/or to help maintain an open capillary structure within the absorbent member to enhance planar transport of liquids away from the area of typical liquid deposition to the rest of the absorbent member. In addition, the particle size distribution of the absorbent gelling material is controlled to improve absorbent capacity and efficiency of the particles employed in the absorbent member. The mixture of hydrophilic fibrous material and relatively large particles of absorbent gelling material in combination with a relatively low density and basis weight acquisition zone provides an improved absorbent member.

The present invention also relates to dual-layer absorbent cores of the type having an absorbent acquisition core which consists essentially of hydrophilic fibrous material and an absorbent member which consists of a mixture of hydrophilic fibrous material and discrete particles of absorbent gelling material having particular particle size distributions. The absorbent member has a top surface area which is from about 0.25 to about 1.0 times the top surface area of the absorbent acquisition core. The absorbent member is further positioned relative to the backsheet of the absorbent article in which its positioned such that at least about 75% of the absorbent gelling material is found within the front two-thirds portion of the absorbent article. The acquisition zone of the absorbent member is also positioned relative to the backsheet such that it is completely positioned within the front two-thirds portion of the absorbent article.

DETAILED DESCRIPTION OF THE DRAWINGS

While the specification concludes with claims which particularly point out and distinctly claim the subject matter regarded as forming the present invention, it is believed the invention will be better understood from the following description taken in conjunction with the accompanying drawings in which:

FIG. 6 is a perspective view of a dual-layer absorbent core having a further alternative embodiment of the absorbent member of the present invention;

FIG. 7 is a sectional view of the dual-layer absorbent core of FIG. 6 taken along sectional line 7—7 of FIG. 6;

FIG. 8 is a plan view of a still further alternative embodiment of the absorbent member of the present invention;

DETAILED DESCRIPTION OF THE INVENTION

Figure 1:
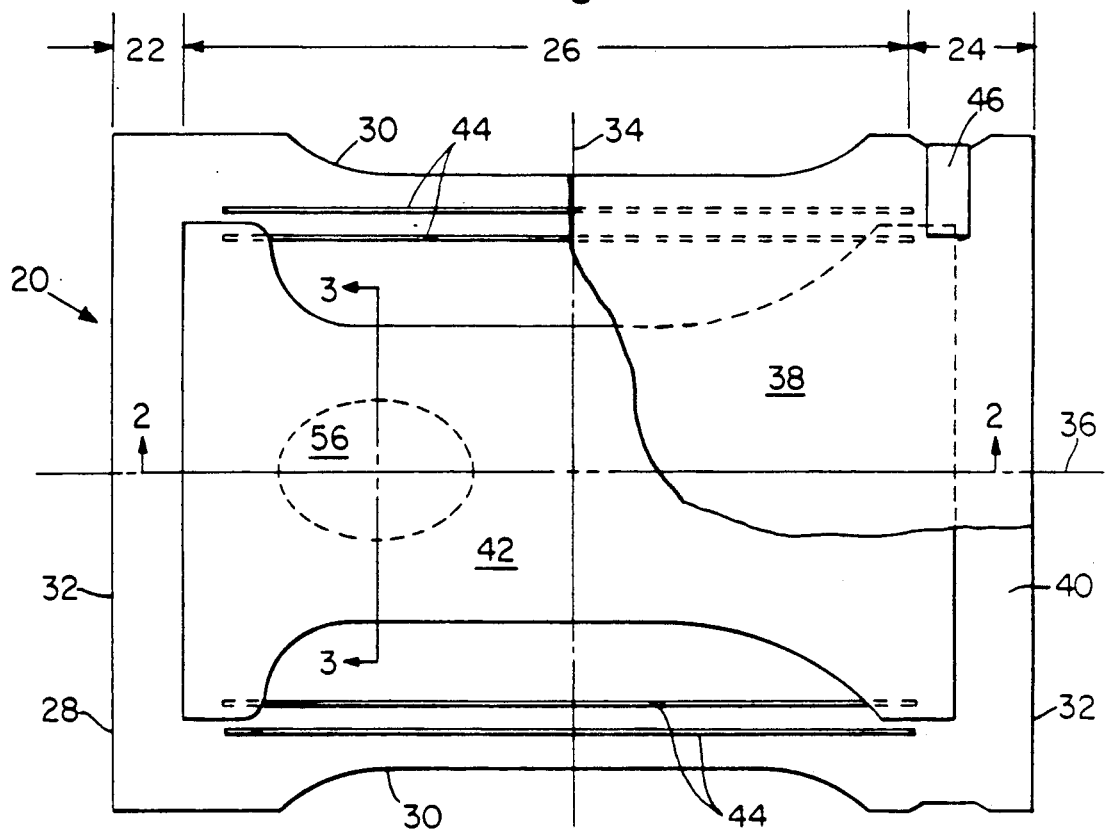
FIG. 1 is a plan view of a disposable diaper embodiment of the present invention wherein most of the topsheet has been cut-away to more clearly show the underlying absorbent member of the diaper.

The absorbent members of the present invention will be described herein in relationship to their use in disposable absorbent articles; however, it should be understood that the potential application of the absorbent members of the present invention should not be limited to disposable absorbent articles. As used herein, the term "disposable absorbent article" refers to articles which absorb and contain body exudates and more specifically refers to articles which are placed against or in proximity to the body of the wearer to absorb and contain the various exudates discharged from the body, and which are intended to be discarded after a single use (i.e., they are not intended to be laundered or otherwise restored or reused). A preferred embodiment of a disposable absorbent article, diaper 20, is shown in FIG. 1. As used herein, the term "diaper" refers to a garment generally worn by infants and incontinent persons that is worn about the lower torso of the wearer. It should be understood, however, that the present invention is also applicable to other disposable absorbent articles such as incontinent briefs, incontinent pads, sanitary napkins, and the like.

FIG. 1 is a plan view of the diaper 20 of the present invention in its flat-out, uncontracted state (i.e., with all elastic induced contraction removed) with portions of the structure being cut-away to more clearly show the construction of the diaper 20 and with the portion of the diaper 20 which contacts the wearer facing the viewer. The diaper 20 is shown in FIG. 1 to have a front waistband region 22, a back waistband region 24, a crotch region 26 and a periphery 28 which is defined by the outer edges of the diaper in which the longitudinal edges are designated 30 and the end edges are designated 32. The diaper additionally has a transverse centerline which is designated 34 and a longitudinal centerline which is designated 36.

The diaper 20 comprises a liquid pervious topsheet 38; a liquid impervious backsheet 40; an absorbent member 42; and elastic members 44. While the topsheet 38, the backsheet 40, the absorbent member 42, and the elastic members 44 may be assembled in a variety of well known configurations, a preferred diaper configuration is described generally in U.S. Pat. No. 3,860,003 entitled "Contractable Side Portions for Disposable Diaper", which issued to K. B. Buell on Jan. 14, 1975, and which patent is incorporated herein by reference.

FIG. 1 shows a preferred embodiment of the diaper 20 in which the topsheet 38 and the backsheet 40 are co-extensive and have length and width dimensions generally larger than those of the absorbent member 42. The topsheet 38 is associated with and superimposed on the backsheet 40 thereby forming the periphery 28 of the diaper 20. The periphery 28 defines the outer perimeter or the edges of the diaper 20. The periphery 28 comprises the end edges 32 and the longitudinal edges 30.

The diaper 20 has front and back waistband regions 22 and 24, respectively, extending from the end edges 32 of the diaper periphery 28 toward the transverse centerline 34 of the diaper a distance from about 2% to about 10%, preferably about 5%, of the length of the diaper 20. The waistband regions comprise those upper portions of the diaper 20, which when worn, encircle the waist of the wearer. The crotch region 26 is that portion of the diaper 20 between the waistband regions 22 and 24, and comprises that portion of the diaper 20 which, when worn, is positioned between the legs of the wearer and covers the lower torso of the wearer. Thus, the crotch region 26 defines the area of typical liquid deposition for a diaper 20 or other disposable absorbent article.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent member 42.

A particularly preferred topsheet 38 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which may be used to manufacture the topsheet 38. For example, the topsheet 38 may be woven, non-woven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross-machine direction.

The backsheet 40 is impervious to liquids and is preferably manufactured from a thin plastic film, although other flexible liquid impervious materials may also be used. The backsheet 40 prevents the exudates absorbed and contained in the absorbent member 42 from wetting articles which contact the diaper 20 such as bed sheets and undergarments. Preferably, the backsheet 40 is polyethylene film having a thickness of from about 0.012 mm (0.5 mil) to about 0.051 millimeters (2.0 mils), although other flexible, liquid impervious materials may be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent member 42 while still preventing exudates from passing through the backsheet 40.

The size of the backsheet 40 is dictated by the size of the absorbent member 42 and the exact diaper design selected. In a preferred embodiment, the backsheet 40 has a modified hourglass-shape extending beyond the absorbent member 42 a minimum distance of at least about 1.3 centimeters to about 2.5 centimeters (about 0.5 to about 1.0 inch) around the entire diaper periphery 28.

The topsheet 38 and the backsheet 40 are associated together in any suitable manner. As used herein, the term "associated" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery 28 by attachment means (not shown) such as an adhesive or any other attachment means as known in the art. For example, a uniform continuous layer of adhesive, a patterned layer of adhesive, or an array of separate lines or spots of adhesive may be used to affix the topsheet 38 to the backsheet 40.

Tape tab fasteners 46 are typically applied to the back waistband region 24 of the diaper 20 to provide a fastening means for holding the diaper on the wearer. Only one of the tape tab fasteners is shown in FIG. 1. The tape tab fasteners 46 can be any of those well known in the art, such as the fastening tape disclosed in U.S. Pat. No. 3,848,594 issued to K. B. Buell on Nov. 19, 1974, which patent is incorporated herein by reference. These tape tab fasteners 46 or other diaper fastening means, such as pins, are typically applied near the corners of the diaper 20.

The elastic members 44 are disposed adjacent the periphery 28 of the diaper 20, preferably along each longitudinal edge 30, so that the elastic members 44 tend to draw and hold the diaper 20 against the legs of the wearer. Alternatively, the elastic members 44 may be disposed adjacent either or both of the end edges 32 of the diaper 20 to provide a waistband as well as or rather than leg cuffs. For example, a suitable waistband is disclosed in U.S. Pat. No. 4,515,595 issued to David J. Kievit and Thomas F. Osterhage on May 7, 1985, which patent is herein incorporated by reference. In addition, a method and apparatus suitable for manufacturing a disposable diaper having elastically contractible elastic members is described in U.S. Pat. No. 4,081,301 entitled "Method and Apparatus for Continuously Attaching Discrete, Stretched Elastic Strands to Predetermined Isolated Portions of Disposable Absorbent Products" which issued to K. B. Buell on Mar. 28, 1978 and which patent is incorporated herein by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 may be stretched and secured while the diaper 20 is in an uncontracted condition. Alternatively, the diaper 20 may be contracted, for example, by pleating, and the elastic members 44 secured and connected to the diaper 20 while the elastic members 44 are in their unrelaxed or unstretched condition.

In the embodiment illustrated in FIG. 1, the elastic members 44 extend essentially the entire length of the diaper 20 in the crotch region 26. Alternatively the elastic members 44 may extend the entire length of the diaper 20, or any other length suitable to provide an elastically contractable line. The length of the elastic members 44 is dictated by the diaper's design.

The elastic members 44 may take a multitude of configurations. For example, the width of the elastic members 44 may be varied from about 0.25 millimeters (0.01 inches) to about 25 millimeters (1.0 inch) or more; the elastic members 44 may comprise a single strand of elastic material or may comprise several parallel or non-parallel strands of elastic material; or the elastic members 44 may be rectangular or curvilinear. Still further, the elastic members 44 may be affixed to the diaper in any of several ways which are known in the art. For example, the elastic members 44 may be ultrasonically bonded, heat and pressure sealed into the diaper 20 using a variety of bonding patterns or the elastic members 44 may simply be glued to the diaper 20.

The absorbent member 42 is positioned between the topsheet 38 and the backsheet 40 to form the diaper 20. The absorbent members of the present invention are fibrous webs or batts which comprise both entangled masses of fibers and particles of absorbent gelling material. The absorbent member 42 is generally compressible, conformable, non-irritating to the wearer's skin, and capable of absorbing and retaining liquids and certain body exudates. It should be understood that for purposes of this invention that an absorbent member is not necessarily limited to a single layer or sheet of material. Thus, the absorbent member 42 may actually comprise laminates or combinations of several sheets or webs of the requisite types of materials as hereinafter described. Thus as used herein, the term "member" includes the term "members" or "layers" or "layered."

Figure 4:
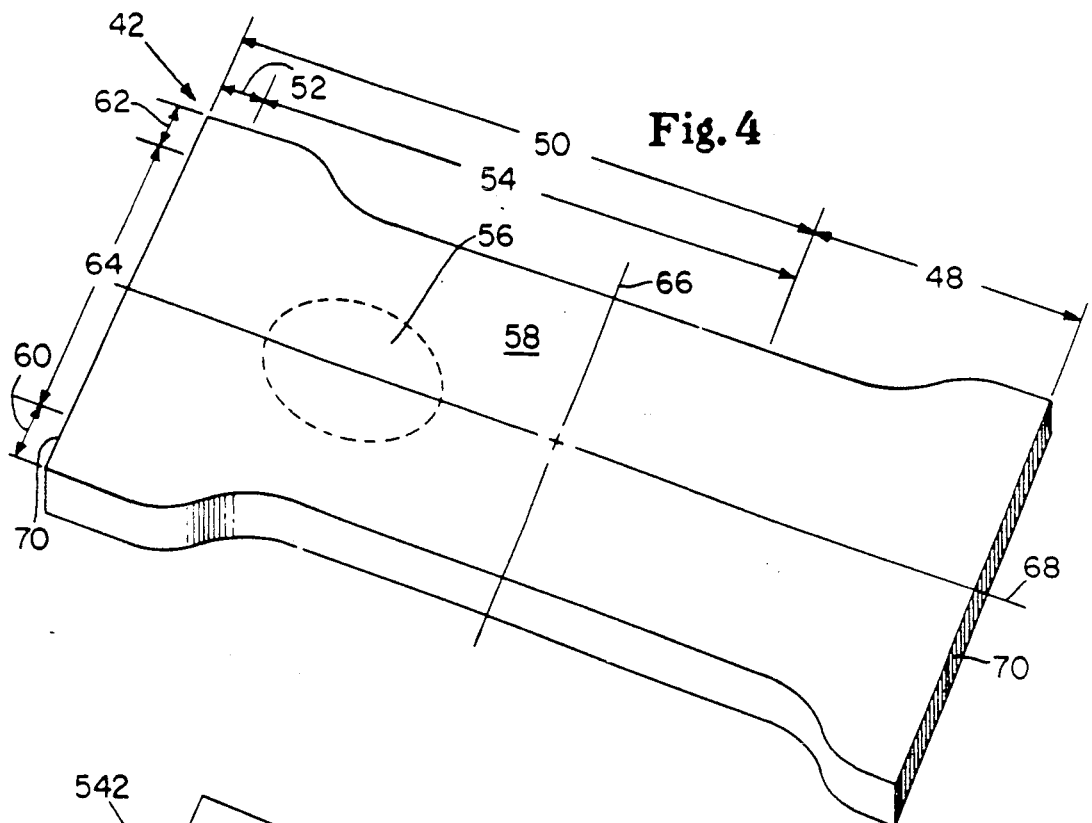
FIG. 4 is a perspective view of the absorbent member of the disposable diaper shown in FIG. 1.

FIG. 4 is a perspective view of a preferred embodiment of the absorbent member 42 of the present invention. The absorbent member 42 is shown in FIG. 4 to comprise a back section 48 and a front section 50. The front section 50 is shown to have an end region 52 and a deposition region 54. The deposition region 54 comprises an acquisition zone 56 (shown by the dotted lines) and a storage zone 58. Further, the front section 50 is transversely divided into three regions comprising two transversely spaced ear regions 60 and 62 respectively, and a central region 64. The absorbent member 42 additionally has a transverse centerline which is designated 66 and a longitudinal centerline which is designated 68.

The absorbent member 42 has a back section 48 and a front section 50 that is contiguous with the back section 48. The back section 48 and the front section 50 of the absorbent member 42 extend respectively from the end edges 70 of the absorbent member 42 toward the transverse centerline 66, the front portion 50 extending a distance from about one half to about three-fourths, preferably about two-thirds, of the length of the absorbent member 42. The front section 50 is preferably greater than one half of the total length of the absorbent member 42 so that it will encompass all of the area of typical liquid deposition of an absorbent member 42 when it is placed in a diaper or other absorbent article.

The front portion 50 has an end region 52 and a deposition region 54. The end region 52 comprises that portion of the front section 50 extending from the respective end edge 70 of the absorbent member 42 toward the transverse centerline 66 a distance from about 2% to about 10%, preferably about 5%, of the length of the absorbent member 42. The deposition region 54 comprises that portion of the front portion 50 that is contiguous with and positioned between the end region 52 and the back section 48 and encompasses the area of typical liquid deposition of the absorbent member 42.

The front portion 50 further has two transversely spaced ear regions 60 and 62 respectively, and a central region 64 disposed intermediate the ear regions 60 and 62. The ear regions 60 and 62 comprise those portions which generally extend from the longitudinal edges 30 of the periphery 28 toward the longitudinal centerline a distance from about one-tenth to about one-third of the width of the absorbent member 42. Thus, the ear regions 60 and 62 are those portions that engage the side marginal portions of the wearer's waist and torso, whereas the central region 64 engages the medial portion of the wearer's waist and torso. The central region thus defines the transverse area of typical liquid deposition.

The absorbent member 42 may be manufactured in a wide variety of sizes and shapes (e.g., rectangular, hourglass, asymmetrical, etc.) and from a wide variety of materials. The total absorbent capacity of the absorbent member 42 should, however, be compatible with the design liquid loading for the intended use of the absorbent article or diaper. Further, the size and absorbent capacity of the absorbent member 42 may be varied to accommodate wearers ranging from infants through adults. The absorbent member 42 preferably comprises a mixture of hydrophilic fibrous material and particular amounts of discrete particles of absorbent gelling material having a particular particle size distribution.

Various types of hydrophilic fibrous material can be used in the absorbent member 42. Any type of hydrophilic fibrous material which is suitable for use in conventional absorbent products are suitable for use in the absorbent member 42 of the present invention. Specific examples of such hydrophilic fibrous material include cellulose fibers, modified cellulose fibers, rayon, polyester fibers such as polyethylene terephthalate (DACRON), hydrophilic nylon (HYDROFIL), and the like. Other examples of suitable hydrophilic fibrous materials include hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. (These structures provide excellent wicking properties which are important in the present invention.) For reasons of availability and cost, cellulose fibers, in particular wood pulp fibers which are also referred to as airfelt, are preferred.

Other cellulosic fiber materials which may be especially useful in certain absorbent members herein are the stiffened, twisted, curled, cellulosic fibers which can be produced by internally cross-linking cellulose fibers with a cross-linking agent. Fibers of this general type are disclosed, for example, in Bernardin, U.S. Pat. No. 3,224,926, issued Dec. 21, 1965; Steiger, U.S. Pat. No. 3,241,553, issued Mar. 22, 1966; Chung, U.S. Pat. No. 3,440,135, issued Apr. 22, 1969; Steiger, U.S. Pat. No. 3,658,613, issued Apr. 26, 1972; Chatterjee, U.S. Pat. No. 3,932,209, issued Jan. 13, 1976 and Sangenis et al., U.S. Pat. No. 4,035,147, issued Jul. 12, 1977, all of which patents are incorporated herein by reference.

One especially preferred type of stiffened, twisted, curled cellulose fibers useful as the hydrophilic fiber component of the absorbent members herein comprises cellulose fibers which have been internally crosslinked, for example with a $C_2$–$C_8$ dialdehyde, while such fibers are in a relatively dehydrated state. Such fibers can be defined in terms of their dry fiber and wet fiber twist counts (at least 4.5 twist nodes per millimeter dry and at least 0.5 twist node per millimeter less than that when wet and preferably also at least about 3.0 twist nodes per millimeter wet) and by their fluid retention characteristics (average isopropyl alcohol retention value of less than 30%; average water retention value of from 28% to 50%). Stiffened, twisted, curled cellulosic fibers of this type are described in greater detail in European Patent Publication No. 251,676; published Jan. 7, 1988 and in European Patent Publication No. 252,650; published Jan. 13, 1988. Both of these published patent applications were filed in the name of The Procter & Gamble Company and both are incorporated herein by reference.

As used herein, the term "hydrophilic" describes fibers or the surfaces of fibers which are wetted by the liquids deposited onto the fibers. The state of the art respecting wetting of materials allows definition of hydrophilicity (and wetting) in terms of contact angles and the surface tension of the liquids and solids involved. This is discussed in detail in The American Chemical Society publication entitled *Contact Angle, Wetability, and Adhesion* edited by Robert F. Gould and copyrighted in 1964. A fiber or surface of a fiber is said to be wetted by a liquid either when the contact angle between the liquid and the fiber or surface is less than 90° or when the liquid will tend to spread spontaneously across the surface of the fiber; both conditions normally coexisting.

In addition to hydrophilic fibrous material, the absorbent member 42 also contains particular amounts of discrete, preferably nonfragile, nonfibrous particles of absorbent gelling material. (Nonfibrous particles being used herein to designate a specific type of "particulate" material wherein the length to diameter ratio of such particulate material is about 10 or less.) Absorbent gelling materials are those materials which, upon contact with liquids, imbibe such liquids and thereby form hydrogels. In this manner, liquids discharged into the absorbent members of the present invention can be acquired and held by the particles, thereby providing absorbent members with enhanced absorbent capacity and/or improved liquid retention performance.

The absorbent gelling material particles which are employed will generally comprise a substantially water-insoluble, slightly cross-linked, partially neutralized, hydrogel-forming polymer material. Such absorbent gelling materials can be prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Suitable unsaturated acidic monomers for use in preparing the absorbent gelling materials used in this invention include those listed in U.S. Pat. No. 4,654,039, entitled "Hydrogel-Forming Polymer Compositions For Use In Absorbent Structures" which issued to Kerryn A. Brandt, Stephen A. Goldman and Thomas A. Inglin on Mar. 31, 1987, and in its allowed Reissue Application Ser. No. 060,718, filed Jun. 10, 1987, both of which are incorporated herein by reference. Preferred monomers include acrylic acid, methacrylic acid, and 2-acrylamido-2-methyl propane sulfonic acid. Acrylic acid itself is especially preferred for preparation of the absorbent gelling material.

In the hydrogel-forming absorbent gelling material the polymeric component formed from unsaturated, acid-containing monomers may be grafted onto other types of polymer moieties such as starch or cellulose. Acrylic acid grafted starch materials of this type are also especially preferred for use herein.

Preferred absorbent gelling materials which can be prepared from conventional types of monomers include hydrolyzed acrylonitrile grafted starch, acrylic acid grafted starch, polyacrylates, maleic anhydride copolymers and combinations thereof. Especially preferred are the polyacrylates and acrylic acid grafted starch.

Whatever the nature of the basic polymer components of the absorbent gelling materials used in the absorbent members herein, such materials will in general be slightly cross-linked. Cross-linking serves to render the absorbent gelling materials used in this invention substantially water-insoluble, and cross-linking thus in part determines the gel volume and extractable polymer characteristics of the hydrogels formed from the absorbent gelling material employed. Suitable cross-linking agents are well known in the art and include, for example, those described in greater detail in U.S. Pat. No. 4,076,663, which issued to Masuda et al. on Feb. 28, 1978, which is incorporated herein by reference. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent can generally comprise from about 0.001 mole percent to 5 mole percent of the resulting absorbent gelling material. More preferably, the cross-linking agent will comprise from about 0.01 mole percent to 3 mole percent of the absorbent gelling material used herein.

The slightly cross-linked, absorbent gelling materials which may be used in the structures of the present invention are generally employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization." Degree of neutralization will preferably not exceed 98%.

The absorbent gelling materials used in the absorbent members herein must have a relatively high capacity for imbibing fluids encountered in absorbent members. The absorbent capacity of such materials can be quantified by referencing the "gel volume" of the polymeric gelling agents which are to be selected for use in the present invention.

For purposes of this invention, gel volume can be defined in terms of the amount of synthetic urine absorbed by any given absorbent gelling material and is specified as grams of synthetic urine per gram of absorbent gelling material. Gel volume in synthetic urine can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. Using a procedure described in greater detail in the Test Methods section of the hereinbefore-referenced U.S. Pat. No. 4,654,039 and its Reissue Application Ser. No. 060,718, the gel volume of the absorbent gelling material in grams of synthetic urine per gram of absorbent gelling material is then calculated from the weight fraction of the absorbent gelling material in the suspension and the ratio of the liquid volume excluded from the formed hydrogel to the total volume of the suspension. (The grams of absorbent gelling material or hydrogel-forming polymer being corrected to a dry weight basis in the calculation of the gel volume.)

The absorbent members of the present invention, and especially the ones which are to be used in diapers, adult incontinence products or training pants, will generally employ absorbent gelling material having a gel volume of at least about 20 grams of synthetic urine per gram of absorbent gelling material. When the absorbent members herein are constructed from cellulosic fibers such as wood pulp fibers, it may be desirable to utilize absorbent gelling material having a somewhat higher gel volume, i.e., a gel volume between about 25 and 60 grams of synthetic urine per gram of gelling agent.

Absorbent members constructed from certain types of cellulosic fiber material such as, for example, the stiffened, curled cellulosic fibers hereinbefore described may actually be more effective at absorbing fluid if absorbent gelling materials of somewhat lower gel volumes are employed. Absorbent gelling material of generally lower gel volume tends to form hydrogels of generally higher gel strength (as quantified by the shear modulus in the manner described in the hereinbefore-referenced U.S. Pat. No. 4,654,039). Thus, in absorbent members wherein the hydrophilic fibers are stiffened, curled cellulose fibers, it may be preferable to employ absorbent gelling material having a gel volume of from about 20 to 35 grams of synthetic urine per gram of absorbent gelling material.

Another feature of the absorbent gelling materials which are especially useful in the absorbent members herein relates to the level of extractable polymer material present in such absorbent gelling material. Extractable polymer levels can be determined by contacting a sample of absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the absorbent gelling materials used herein is also set forth in the hereinbefore referenced U.S. Pat. No. 4,654,039 and its Reissue Application Ser. No. 060,718. Absorbent gelling materials especially useful in the absorbent members herein are those which have an equilibrium extractables content in synthetic urine of no more than about 17%, preferably no more than about 10% by weight of the absorbent gelling material.

Although most absorbent gelling materials will perform well in the absorbent member 42 of the present invention, absorbent gelling materials having high gel strength are particularly useful. Gel strength must be such that the particles of absorbent gelling material do not deform and fill to an unacceptable degree the capillary void space in the absorbent member 42, thereby inhibiting both absorbent capacity of the structure and fluid distribution throughout the structure.

Gel strength refers to the tendency of the particles of absorbent gelling material to deform or spread under stress once the particles absorb liquids. For a given type of absorbent gelling material, gel strength will generally decrease as the gel volume increases. It has been found that it is desirable to utilize an absorbent member 42 whose polymer materials have as high a gel strength as possible consistent with the realization of absorbent gelling materials of acceptably high gel volume.

It has been found that gel strength, i.e., gel deformation tendency, (in the context of absorbent gelling materials incorporated into absorbent members and absorbent articles) correlates directly with the shear modulus of the absorbent gelling material. Accordingly, polymer materials of absorbent gelling material having sufficient gel strength can be appropriately characterized by specifying gel strength in terms of the shear modulus of the particles of absorbent gelling material.

Shear modulus can be conventionally measured, for example, by a procedure which involves the use of a stress rheometer to determine the ratio of (a) stress applied to a given sample versus (b) the resulting strain exhibited by the sample. The absorbent gelling material sample tested in this manner is swollen to its gel volume with synthetic urine. Using a procedure described in greater detail hereinafter, the stress/strain ratio is determined. The shear modulus of the resulting sample in $dynes/cm^2$ is then subsequently calculated from this ratio. Absorbent gelling materials which have been found to be particularly useful in the present invention exhibit a shear modulus of at least about 2,000 $dynes/cm^2$. More preferably, the absorbent gelling materials have a shear modulus within the range of about 2,500 to about 92,000 $dynes/cm^2$ and most preferably of from about 5,000 to about 35,000 $dynes/cm^2$.

Without wishing to be bound by any particular theory, it is believed that absorbent gelling materials having high gel strength as reflected in their shear modulus values will resist deformation upon fluid absorption and will have a reduced tendency to flow into the void spaces between fibers. Thus, high gel strength absorbent gelling materials may actually serve to maintain or increase separation of the individual fibers of the hydrophilic fibrous material. Such fiber separation improves both the wicking and the absorbent capacity of such absorbent members. Low gel strength materials, on the other hand, merely flow into the void spaces between the fibers upon fluid absorption and can thereby actually reduce the acquisition rate and the absorbent capacity of the absorbent members and absorbent articles into which they are incorporated.

Gel strength of absorbent gelling materials is quantified by means of determining the shear modulus of a sample of the swollen particles. Shear modulus is determined using a stress rheometer which comprises a circular lower plate onto which the swollen particle sample is placed. A truncated conical upper element having the same projected surface area as the area of the lower circular plate is positioned above the circular lower plate. This upper element is lowered into the mass of swollen particle material on the circular lower plate and is positioned at the proper gap relative to the circular lower plate. This gap corresponds to the point at which an untruncated cone would contact the lower plate.

An oscillating torque (stress) is applied torsionally to the conical element, and the resulting angular displacement of the cone is determined as a function of the applied torque.

The sample being tested is swollen to its gel volume in synthetic urine. Synthetic Urine is typically 15.0 parts of 1% Triton X-100, 60.0 parts of NaCl, 1.8 parts of $CaCl_2 \cdot 2H_2O$, and 3.6 parts of $MgCl_2 \cdot 6H_2O$, diluted to 6000 parts with distilled $H_2O$. The resulting solution has an absorbence of about 0.25 at its absorbence maximum of 617 mm.

Excess free synthetic urine is removed from the sample by blotting, and approximately 1.5 cc of the swollen material is placed in the gap between the lower circular plate and the upper conical element of the rheometer. This mass is usually formed from an agglomeration of swollen particles which have unswollen particle dimensions less than 710 microns. Spherical particles should be ground to form irregular shaped particles before testing.

Stress and strain measurements are taken under the following conditions:

| Parameter | Value |
| --- | --- |
| Type of Rheometer | Sangamo Visco-elastic Analyzer |
| Configuration | Oscillating Cone and Plate |
| Plate Radius | 2.5 cm |
| Cone Radius (Edge to vertex) | 2.5 cm |
| Cone Angle* | 43.6 milliradians |
| Oscillation Frequency | 1.0 Hertz |
| Strain Amplitude | 2.5% |
| Sample Temperature | 21.4° C. |

*Angle between surface of the lower plate and the surface of the cone i.e., (Pi/2 - semi-vertical angle.)

Under these conditions, an oscillatory torque (stress) is applied via the upper conical element to the swollen particles. This results in an oscillatory response (strain) of the sample which is reflected by the magnitude of the angle through which the conical element rotates in response to the applied torque. The shear modulus of the particles is calculated from the ratio of (i) the applied stress to (ii) the amplitude of the in-phase component of the resultant strain.

For the particular cone/plate geometry employed in this testing, the ratio of stress (g-cm) to strain (milliradians) is converted to shear modulus (dynes/cm$^2$) using the following formula:

$$\text{Shear Modulus} = \frac{3 \times 981 \times \text{Cone Angle} \times \text{Cos(Phase Angle)} \times \text{Torque}}{2 \times \text{Pi} \times \text{Plate Radius}^3 \times \text{Strain}}$$

wherein the cone angle and strain are expressed in units of milliradians, the plate radius in units of cm and torque in units of g-cm. For absorbent gelling materials, the phase angle is close to zero and so the cosine of the phase angle is taken as unity. The factor 981 is that which converts g-cm to dyne-cm. Thus $$\text{Shear Modulus (dynes/cm}^2\text{)} = 1308 \times \frac{\text{Torque (gm-cm)}}{\text{Strain (milliradians)}}$$

for the particular equipment used in this test method.

An important feature of the present invention is the utilization of the above-described absorbent gelling materials in the absorbent member in the form of nonfibrous, preferably nonfragile, particles having certain particle size characteristics. In particular, it has been discovered that an unexpected improvement in absorbent capacity, acquisition, and distribution within the absorbent member can be realized by incorporating absorbent gelling material into the particular absorbent members of the present invention in the form of particles which are generally larger than those which have heretofore been conventionally employed. Generally, provision of particles of absorbent gelling material of this relatively larger size requires the use of one or more manufacturing or processing techniques which eliminate or reduce the amount of smaller, finer particles and/or create larger particles that are introduced, along with the fibrous material, into the absorbent members herein. An upper limit on absorbent gelling material particle size can also be provided since gelling agent particles which are too large are less desirable from a consumer aesthetics standpoint.

Specifically, the present invention requires the utilization in the absorbent members herein of absorbent gelling material particles of a selected mass median particle size and a certain particle size deviation from the mass median particle size. For purposes of the present invention, particle size is defined as the dimension of a particle which is determined by sieve size analysis. Thus, for example, in principle, a particle that is retained on a sieve with 707 micron openings is considered to have a particle size greater than or equal to 707 microns; a particle that passes through a sieve with 707 micron openings and is retained on a sieve with 500 micron openings is considered to have a particle size between 500 and 707 microns; and a particle that passes through a sieve with 500 micron openings is considered to have a particle size less than 500 microns.

Further, for purposes of this invention, the mass median particle size of a given sample of absorbent gelling material particles is defined as the particle size which divides the sample in half on a mass basis, i.e., half of the sample by weight will have a particle size greater than the mass median particle size and half of the sample by weight will have a particle size less than the mass median particle size. Thus, for example, the mass median particle size of a sample of absorbent gelling material particles is 500 microns if one half of the sample by weight is retained on a sieve with openings of 500 microns. A standard particle-size plotting method (wherein cumulative weight percent of the particle sample retained on or passed through a given sieve size is plotted versus sieve-opening size on probability paper) is typically used to determine mass median particle size when the 50% mass value does not correspond to the size opening of a U.S.A. Standard Testing Sieve. A plot of this type is also typically used to determine the distribution of particle size about the mass median value.

The absorbent gelling material particles employed in the absorbent member of the present invention must have a mass median particle size greater than or equal to about 400 microns. Preferably, the mass median particle size of the particles will be greater than or equal to about 420 microns. More preferably, the mass median particle size of the particles will be greater than or equal to about 500 microns. Because very large particles are less desirable from a consumer aesthetics viewpoint, the mass median particle size may have an upper limit such that the mass median particle size is expressed in terms of a range. Thus, preferred mass median particle sizes range from about 400 to about 1680 microns, more preferably from about 400 to about 1410 microns, most preferably from about 400 to about 1190 microns.

Preferably, the absorbent gelling material particles used will also have a certain maximum particle size deviation from the mass median particle size. In particular, it is preferred that no more than about 16% by weight of the absorbent gelling material particles have a particle size less than 200 microns and/or no more than about 16% by weight of these particles have a particle size greater than 1680 microns. More preferably, no more than about 16% by weight of these particles should have a particle size less than 210 microns and/or no more than about 16% by weight have a particle size greater than 1410 microns, most preferably no more than about 16% by weight have a particle size greater than about 1190 microns.

In an especially preferred embodiment of the present invention, the particles of absorbent gelling material will have a mass median particle size greater than or equal to about 841 microns. Particles having a mass median particle size greater than or equal to about 841 microns are especially preferred for use in the present invention because they provide larger capillaries within the absorbent member to enhance planar wicking and are generally slower absorbing on a mass basis so as to provide higher gush capacity for the absorbent member. Preferably, the mass median particle size should range from about 841 microns to about 1680 microns, more preferably from about 841 microns to about 1410 microns, with a range from about 841 microns to about 1190 microns being most preferred. The particles of absorbent gelling material also, preferably, have a certain maximum size deviation from the mass median particle size. In particular, it is preferred that between 0% and about 20% by weight of the particles have a particle size less than about 841 microns. More preferably, between 0% and about 10%, and most preferably between 0% and about 5%, of the particles have a particle size less than about 841 microns.

Within the foregoing mass median particle size and particle size distribution limitations, it is possible to further identify preferred particle size characteristics for the gelling agent particles useful herein by means of standard sieve analyses. In a typical sieve analysis, a sample or plurality of gelling agent particles is sifted through a set number of screens of diminishing screen opening size and the weight percent of the sample retained on and/or passing through each screen is determined. Standard methods for making such sieve analyses have been established, for example, by the American Society for Testing Materials (ASTM). One such method employs a Ro-Tap testing sieve shaker (manufactured by W. S. Tyler, Inc.) and a series of screens identified by either U.S. Sieve Series or Tyler Standard Sieve Series designations. Determination of particle size distribution using such a technique is described in greater detail in *Perry's Chemical Engineers' Handbook, Sixth Edition*, (McGraw-Hill Book Company, 1984) at pp. 21-13 to 21-19, which publication is incorporated herein by reference.

The absorbent gelling material particles can be adjusted to, or close to, the requisite particle size distribution by controlling the processing techniques used to prepare the absorbent gelling material. Frequently this will involve varying and monitoring the conditions under which the absorbent gelling material is polymerized, dried, chopped, ground and/or agglomerated. Once absorbent gelling material particles are formed by whatever process, further treatment such as screening may be required to remove particles which, if left in, would cause the absorbent gelling material particle component to fall outside of the hereinbefore-described particle size requirements.

One preferred technique for preparing particles which are larger than those ordinarily prepared by absorbent gelling material polymerization-drying-chopping techniques involves agglomeration of smaller particles to produce larger agglomerates. Agglomeration techniques can thus be used to raise the mass median particle size of absorbent gelling material particles and to thereby provide particles in agglomerated form which are suitable for use in the absorbent members herein. Agglomeration techniques are well known in the art and may or may not involve the use of moisture addition to smaller particles or the use of a binder or other type of agglomerating medium.

Absorbent gelling material particles used in the absorbent members herein, whether or not in agglomerated form, should be nonfragile. For purposes of the present invention, such particles are nonfragile if they are stable enough to withstand the forces encountered in manufacture and/or use without breaking apart and completely separating into their smaller component particles. This means that the particles should be stable enough that they do not break apart into smaller particles to the extent that the resulting particles would fall outside the scope of the particle size limitations set herein.

The relative amount of hydrophilic fibrous material and particles of absorbent gelling material used in the absorbent member 42 of the present invention can be most conveniently expressed in terms of a weight percentage of the absorbent member 42. The absorbent member 42 preferably contains from about 2% to about 60%, more preferably from about 5% to about 40%, and most preferably from about 10% to about 25% by weight, of the absorbent member 42 of absorbent gelling material. This concentration of absorbent gelling material can also be expressed in terms of a weight ratio of fiber to particulate. These ratios may range from about 40:60 to about 98:2. For most large particle absorbent gelling materials, the optimum fiber-to-particulate weight ratio is in the range of from about 60:40 to about 95:5. Based on a cost/performance analysis, ratios of from about 75:25 to about 90:10 are most preferred for use in the absorbent member 42.

In addition, the particles of absorbent gelling material may be dispersed in various weight ratios throughout different regions and thickness of the absorbent member 42.

For example, the mixture of hydrophilic fibrous material and relatively large particles of absorbent gelling material may be disposed only in the deposition region 54 of the absorbent member 42 and not in the back section 48 or the end region 52 or may be disposed only in the acquisition zone and not in the storage zone. In addition, the acquisition zone 56 need not comprise the fiber/particle mixture such that only the storage zone contains the mixture of fibrous material and absorbent gelling material. While an acquisition zone 56 containing only hydrophilic fibrous material works satisfactorily in rapidly acquiring liquids, without additional acquisition or wicking capacity such an embodiment is not preferred. When relatively large particles of absorbent gelling material are maintained in the acquisition zone 56, the particles help maintain an open capillary structure when the acquisition zone 56 is wetted so as to enhance planar transport of liquids away from the acquisition zone 56 to the rest of the absorbent member 42. In addition, the acquisition rate of the absorbent member is enhanced because, it is believed, relatively large particles acquire liquid more slowly on a mass basis than small particles, such that gel blocking is minimized resulting in the gush capacity of the acquisition zone being enhanced especially, it is believed, for subsequent loadings. Thus, at least the storage zone 58, and preferably both the acquisition zone 56 and the storage zone 58 contains a uniformly distributed mixture of hydrophilic fibrous material and relatively large particles of absorbent gelling material. It is most preferred that the particles are substantially uniformly dispersed (thoroughly dispersed) throughout the entire absorbent member 42, although the relatively large particles may be distributed in regions or zones which have higher concentrations of particles of absorbent gelling material than do other regions or zones. For example, there may be a concentration gradient along the thickness dimension with either the lowest concentration being at or near the surface of the absorbent member which receives liquids (i.e., the top surface) or with the highest concentration being at or near the top surface of the absorbent member, especially in the acquisition zone.

The deposition region 54 comprises an acquisition zone 56 and a storage zone 58 in liquid communication with at least a portion of the acquisition zone 56. The acquisition zone 56 comprises portions of the deposition region 54 designated by the dotted lines in FIG. 4. The storage zone 58 generally comprises the remainder of the deposition region 54 and more preferably the remainder of the absorbent member 42.

It has been found that a relative capillarity difference between the acquisition zone 56 and the storage zone 58 is of importance in the overall efficiency and effectiveness of the absorbent member 42. While liquid capillarity can be defined in several ways (e.g., pore size, density, basis weight, etc.), the density and basis weight of the structure are the preferred parameters to define liquid capillarity in the absorbent member 42 of the present invention. Thus, the acquisition zone 56 must have both a relatively lower average density and lower average basis weight per unit area than the storage zone 48 to establish the preferred capillary force gradient between them. Thus, the ratio of the average density of the storage zone 58 to the average density of the acquisition zone 56 should preferably be about equal to or greater than about 1.25:1, more preferably about 1.5:1 and most preferably about 2:1.

Without wishing to be bound by theory, it is believed that the differential lower capillarity, the lower average density and lower average basis weight, of the acquisition zone 56 in comparison to the storage zone 58 is significant in achieving both a more optimized liquid acquisition rate into the absorbent member 42 and a relatively high liquid planar wicking rate throughout the absorbent member 42. When an absorbent member 42 having a mixture of hydrophilic fibrous material and particles of absorbent gelling material is densified to the densities approximating those of the storage zone 58, the liquid planar wicking rate becomes much faster. It is believed that densifying the absorbent member 42 results in better planar wicking of liquid throughout the absorbent member 42 (the x-y direction) because of the higher capillary force due to the smaller pore size of the densified fibers. Densifying the absorbent member 42 further results in a reduction in the bulk of the structure (which is desirable from a consumer standpoint for aesthetic reasons).

However, the densification of the absorbent member 42 also results in a reduction in the rate of liquid acquisition into the absorbent member 42 in the direction normal to planar wicking (i.e., the z-direction). It is believed that as higher amounts of absorbent gelling material are located in the area of typical liquid deposition, a maximum gel blocking effect is achieved, thereby reducing the liquid acquisition rate. Thus, it is important to provide a means for delivering the liquid into the absorbent member 42 at a high rate. The acquisition zone 56 of lower average density and lower average basis weight per unit area than the densified absorbent member 42 or storage zone 58 provides such a means. The acquisition zone 56 has a smaller amount of particles of absorbent gelling material in the area of typical liquid deposition, thereby reducing the incidence of gel blocking in this area during the liquid acquisition phase and thus improving the liquid acquisition rate.

The capillary force gradient created at the interface between the acquisition zone 56 and the storage area 58 also improves the containment characteristics of the absorbent member 42. Liquids deposited on the acquisition zone 56 tend to be acquired quickly into the structure by the action of the acquisition zone 56. Because the storage zone 58 has a higher capillarity than the acquisition zone 56, the acquired liquids tend to be drawn into the storage zone 58 and are then delivered to the other portions of the storage zone 58 by the enhanced planar wicking rate achieved in the storage zone 58; the liquids being retained even under moderate pressure by the particles of absorbent gelling material in the storage zone 58. Thus, it has been found that an absorbent member 42 having an acquisition zone 56 having a lower average density and lower average basis weight per unit area than the storage zone 58 improves leakage containment by more quickly acquiring and distributing liquids into and throughout the absorbent member 42.

In addition, it is believed that the acquisition zone 56 provides an additional mechanism whereby an absorbent member 42 that has already been wetted may contain and more readily acquire further discharged liquids. A property of the particles of absorbent gelling material is that they expand when wetted. Thus when the absorbent member 42 is wetted, the particles of absorbent gelling material in both the acquisition zone 56 and the storage zone 58 expand. However, because there is a greater amount of particles of absorbent gelling material in the higher average density and higher average basis weight storage zone 58, the storage zone 58 tends to expand to a greater thickness than the acquisition zone 56. Thus, if the acquisition zone 56 is laterally surrounded by the storage zone 58, a well or hole effect is created. This "well" is advantageous for second depositions of liquids because the liquids will tend to be drawn into the well because it is in effect a zero density acquisition area. This is especially helpful in the case of diapers for overnight use wherein the wearer sleeps on the stomach because gravity additionally tends to pull the later discharged liquids into the well whereupon they distribute into the acquisition zone 56 and are wicked into the storage zone 58. Thus, the acquisition zone 56 provides an additional advantage for wetted absorbent members.

The storage zone 58 is thus the relatively high capillarity (high density and high basis weight) portion of at least the deposition region 54. The primary functions of the storage zone 58 are to absorb discharged liquids that are either deposited directly onto the storage zone 58 or transferred to the storage zone 58 via the capillary force gradients established between the acquisition zone 56 and the storage zone 58, and to retain such liquids under the pressures encountered as a result of the wearer's movements. Preferably, the storage zone 58 consists essentially of the structure disclosed in above-referenced U.S. Pat. Nos. 4,610,678 and the lower fluid storage layer disclosed in 4,673,402, both of which are incorporated herein by reference, although other high capillarity structures may also be used.

The storage zone 58 preferably has a relatively high density and a high basis weight in relation to the acquisition zone 56. The density and basis weight values of the storage zone 58 include the weight of the particles of absorbent gelling material, such that the density and basis weight values will vary depending upon the amount of particles dispersed throughout the absorbent member 42. Thus, the storage zone 58 will generally have a density of from about 0.06 to about 0.4 g/cm$^3$, and more preferably within the range of from about 0.09 to about 0.20 g/cm$^3$ for an absorbent member 42 containing about 15% by weight of particles of absorbent gelling material. The basis weight of such a storage zone 58 can range from about 0.02 to about 0.186 g/cm$^2$ preferably from about 0.038 to about 0.12 g/cm$^2$. For an absorbent member 42 containing about 50% by weight of particles of absorbent gelling material, the density will typically range from about 0.1 to about 0.68 g/cm$^3$ with a basis weight from about 0.034 to about 0.31 g/cm$^2$. The density of the storage zone 58 is calculated from its basis weight and caliper measured on newly unpacked, unfolded and dissected diapers. The caliper is measured using a standard gauge with the sample under a "gentle" load of 10 g/cm$^2$. The basis weight is measured by die-cutting a certain size sample and weighing the sample on a standard scale, the weight and area of the sample determining the basis weight. (It should be noted that the density and basis weight values include the weight of the particles of absorbent gelling material.)

Figure 2:
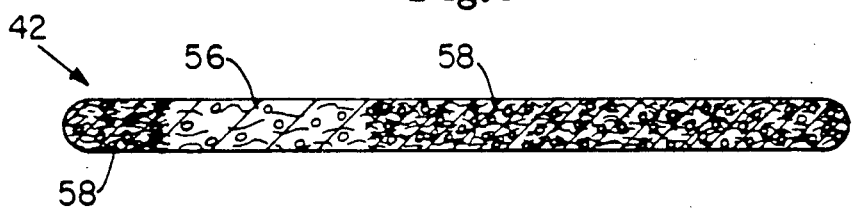
FIG. 2 is a longitudinal sectional view of only the absorbent member of the disposable diaper taken along sectional line 2—2 of FIG. 1.
Figure 3:
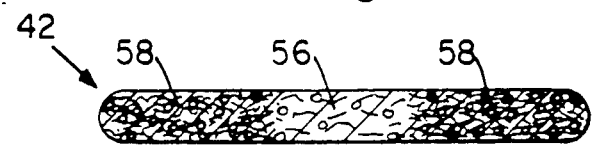
FIG. 3 is a transverse sectional view of only the absorbent member of the disposable diaper taken along sectional line 3—3 of FIG. 1.

While the storage zone 58 may take on a number of sizes and shapes, it is preferred that the storage zone 58 comprises the portion of at least the deposition region 54 wherein there is no acquisition zone 56. (i.e., The entire deposition region 54 comprises a storage zone 58 except for the acquisition zone 56.) While the back section 48 and the end region 52 need not comprise storage zones, in the particularly preferred embodiments of the absorbent member 42 as shown in FIGS. 2, 3 and 4, the entire absorbent member 42 except for the acquisition zone 56 consists of one or more storage zones 58. In addition, while the storage zone 58 need not completely laterally surround the acquisition zone 56 (i.e., it is in liquid communication with at least a portion of the lateral area of the acquisition zone 56), in preferred embodiments of the present invention, the storage zone 58 laterally surrounds the acquisition zone 56 so as to take full advantage of the capillarity difference between them.

The acquisition zone 56 has a relatively lower capillarity and thus preferably a lower average density and a lower average basis weight per unit area than the storage zone 58. The acquisition zone 56 serves to quickly collect and temporarily hold discharged liquids. Since such liquids are generally discharged in gushes, the acquisition zone 56 must be able to quickly acquire and transport liquid by wicking from the point of liquid contact to other parts of the absorbent member 42. The acquisition zone 56 preferably has a density of from about 0.03 to 0.24 g/cm$^3$, more preferably from about 0.05 to about 0.15 g/cm$^3$ for an absorbent member 42 containing about 15% by weight of particles of absorbent gelling material. The basis weight of such an acquisition zone 56 will preferably range from about 0.015 to about 0.1 g/cm$^2$ and more preferably from about 0.018 to about 0.06 g/cm$^2$. For an absorbent member 42 containing about 50% by weight of particles of absorbent gelling material, the density will typically range from about 0.05 to about 0.41 g/cm$^3$ with a basis weight of from about 0.025 to about 0.17 g/cm$^2$. The density of the acquisition zone 56 is calculated from its basis weight and caliper measured on newly unpacked, unfolded and dissected diapers. The caliper is measured using a standard gauge with the sample under a "gentle" load of 10 g/cm$^2$. The basis weight is measured by die-cutting a certain size sample and weighing the sample on a standard scale, the weight and area of the sample determining the basis weight. (The density and basis weight values include the weight of the particles of absorbent gelling material.)

While the acquisition zone 56 may conceivably have density and basis weight values equal to zero, i.e., a hole or void space, such an embodiment is not as preferred as an acquisition zone 56 having some minimal value of density and basis weight. The transfer of liquids through the topsheet 38 has been found to be diminished in an absorbent member 42 having an acquisition zone 56 of zero density and basis weight due to the lack of intimate contact between any fibers of the acquisition zone 56 and the topsheet 38. Thus, liquid may tend to pool or collect on the topsheet 38 thereby creating a wet feeling for the wearer. Thus, it is preferred that the acquisition zone 56 have some minimum density and basis weight.

While the density and basis weight of the acquisition zone 56 may vary throughout its area and thickness, such an embodiment is also not preferred. The acquisition zone 56 preferably has a substantially uniform density and uniform basis weight throughout its area and thickness. This uniform density and basis weight provides a uniform capillary force gradient across the interface between the acquisition zone 56 and the storage zone 58 that provides even liquid transfer.

The shape, size and positioning of the acquisition zone 56 is of importance in determining the effectiveness of the resulting absorbent member 42 in rapidly acquiring discharged liquids. In accordance with the present invention, the acquisition zone 56 should be placed in a specific positional relationship with respect to the area of typical liquid deposition of the absorbent member 42. While portions of the acquisition zone 56 may be positioned in the back section 48 of the absorbent member 42, the acquisition zone 56 is preferably positioned generally in the front section 50 of the absorbent member 42 so that the acquisition zone 56 is positioned in the area of typical liquid deposition, i.e., the deposition region 54. Thus, the acquisition zone 56 is placed in the vicinity of the point of discharge of liquids so as to be capable of quickly acquiring such liquids at their contact zone.

The generally forward positioning of the acquisition zone 56 can be defined by specifying the percentage of the top surface area of the acquisition zone 56 which is found forward of particular points along the length of the absorbent member 42. While the positioning of the acquisition zone 56 can alternatively be defined with respect to the volume of the acquisition zone positioned forward of particular points, it has been found that the top surface area of the acquisition zone 56 is a more desirable definition because the top surface area actually defines the initial area available for liquid acquisition. In addition, since the thickness of the absorbent member 42 is preferably uniform in the deposition region 54 and the acquisition zone 56 has a generally rectangular cross-sectional area, the top surface area definition is equal to a volumetric definition in a preferred embodiment. Thus, the positioning of the acquisition zone 56 will be referenced throughout the specification as related to its top surface area. (i.e., The percentage of the top surface area of the acquisition zone positioned in a given area.)

Thus, in accordance with the present invention, at least a portion of the acquisition zone 56 must be placed in the deposition region 54, even though the remaining portion may be positioned anywhere in the absorbent member 42 including the back section 48 and the end regions 52. (It being understood that if plural acquisition zones are utilized, at least a portion of one of the acquisition zones must be positioned in the deposition region 54.) However, the acquisition zone 56 is preferably positioned relative to the absorbent member 42 such that the top surface area of the acquisition zone 56 is completely positioned within the front section 50 of the absorbent member 42. More preferably, the acquisition zone 56 is positioned relative to the absorbent member 42 such that the top surface area of the acquisition zone 56 is completely positioned within the deposition region 54 of the absorbent member 42. Even more preferably, at least 30% of the top surface area of the acquisition zone 56 is positioned in the front half of the front section (approximately the front $\frac{1}{3}$ of the overall absorbent member 42) of the absorbent member 42.

The forward positioning of the acquisition zone 56 may alternatively be defined by specifying the percentage of the top surface area of the acquisition zone 56 that is found forward of particular points along the length of the diaper 20 or other absorbent article. Thus, the acquisition zone 56 is preferably positioned on the absorbent member 42 relative to the backsheet 40 such that at least a portion of top surface area of the acquisition zone 56 is in the crotch region 26 of the diaper 20. More preferably, the acquisition zone 56 is positioned such that its top surface area is completely positioned in the front two-thirds portion of the diaper 20, most preferably in the front half portion of the diaper 20; the top surface area also most preferably being completely positioned in the crotch region 26 of the diaper 20. (As noted herein, "portions" of the diaper 20 or other absorbent article can be defined by reference to the top surface area of the unfolded diaper 20 or absorbent article found in front of a given point on the line which defines the length of the diaper 20).

For purposes of determining the positioning of such acquisition zone 56; the length of the absorbent member 42 or diaper 20 will be taken as the normal longest longitudinal dimension of the elongated structure. This normal longest dimension can be defined with respect to the structure as it is applied to the wearer. When worn, the opposing ends of the backsheet are fastened together so that the ends form a circle around the wearer's waist. The normal length of the absorbent member 42 or diaper 20 will thus be the length of the line running through the absorbent member 42 or diaper 20 from the point on the edge of it at the middle of the wearer's back waist, through the crotch, to the point on the opposite edge of the absorbent member 42 or diaper 20 at the middle of the wearer's front waist.

The top surface area of the acquisition zone 56 may be found using either of two techniques. The primary and simplest way is to place the absorbent member 42 on a standard light box, such as the transluminator model manufactured by Aristo grid Lamp Products, Inc. The acquisition zone 56, because it has a lower average density and lower average basis weight than the surrounding storage zone 58, will appear lighter or brighter due to the fact that more light will be transmitted through the acquisition zone 56. The acquisition zone 56 can then be mapped onto paper having grids to measure the top surface area of the acquisition zone 56.

The alternative method comprises mapping the density profile of the absorbent member 42 to determine the top surface area of the acquisition zone 56. The absorbent member 42 is cut into samples having small areas. The density and basis weight of each of the samples are then calculated using the techniques discussed above. Thus, the relatively lower density and lower basis weight samples are charted against the relatively higher density and higher basis weight samples to measure the top surface area of the acquisition zone 56.

The acquisition zone 56 can be of any desired shape consistent with the absorbency requirements of the absorbent member 42 or diaper 20 including, for example, circular, rectangular, triangular, trapezoidal, oblong, hourglass-shaped, funnel-shaped, dog-bone-shaped, fox-shaped or oval. Preferred shapes of the acquisition zone 56 are those that increase the perimeter of the interface between the acquisition zone 56 and the storage zone 58 so that the relative capillarity difference between the zones are fully utilized. In the embodiment shown in FIGS. 1-4, the acquisition zone is oval shaped having a top surface area of about 45 cm$^2$ (about 7 in$^2$).

In order to maintain a certain minimal absorbency level in the front section 50 of the absorbent member 42, the top surface area or volume of the storage zone 58 must comprise some minimal amount of the top surface area or volume of the front section 50. Thus, it has been found that the acquisition zone 56 should preferably comprise less than the entire top surface area and/or volume of the front section 50 of the absorbent member 42. (Since in a preferred embodiment the acquisition zone 56 is of generally uniform thickness and cross-sectional area, volume can be interchanged with top surface area as a definitional point.) The top surface area of the portion of the acquisition zone 56 positioned in the front section 50 of the absorbent member 42 preferably comprises less than about 50% of the top surface area of the front section 50. More preferably, the top surface area of the acquisition zone 56 comprises less than about 35% of the top surface area of the front section 50 of the absorbent member 42, with less than about 20% being especially preferred. In addition, the top surface area of the acquisition zone 56 preferably comprises less than about 50% of the top surface area of the deposition region 54, more preferably less than about 35%, and most preferably less than about 20%.

The acquisition zone 56 may also have a number of different cross-sectional areas and configurations including those wherein the area of portions of the acquisition zone 56 is less or greater than its top surface area (i.e., The acquisition zone 56 is smaller or wider below the top surface of the absorbent member 42.) For example, the acquisition zone 56 may have conical, trapezoidal, T-shaped or rectangular cross-sectional areas. As shown in FIGS. 2 and 3, the acquisition zone 56 preferably has a rectangular cross-sectional area so as to provide a uniform acquisition zone 56.

In addition, the acquisition zone 56 need not comprise the entire thickness of the absorbent member 42, but may extend through only a fraction of its total thickness. The acquisition zone 56 may also have a different thickness than the surrounding storage zone 58. However, in a preferred embodiment as shown in FIGS. 2 and 3, the acquisition zone 56 preferably extends through the entire thickness of the absorbent member 42 and has a thickness equal to the thickness of the surrounding storage zone 58 in the deposition region 54.

While the acquisition zone 56 may be transversely positioned anywhere along the absorbent member 42, it has been found that the acquisition zone 56 functions the most efficiently when it is transversely centered within the front section 50 or the deposition region 54 of the absorbent member 42. Thus, the acquisition zone 56 is preferably centered about the longitudinal centerline 68 of the absorbent member 42. More preferably, the acquisition zone 56 is transversely positioned only in the central region 64 of the front section 50 or deposition region 54 of the absorbent member 42 such that none of the acquisition zone 56 is located in the ear regions 60 and 62.

Such an absorbent member 42 is preferably made by airlaying a thickness profiled absorbent member-preform and then calendering the absorbent member 42 in a fixed-gap calender roll to effect densifying the absorbent member 42. The thickness profiled absorbent member 42 initially has areas of higher basis weight which define the storage zone 58 and of lower basis weight which define the aquisition zone 56. The absorbent member 42 is then calendered preferably to at least a uniform thickness in the deposition region. Thus, a lower average density and a lower average basis weight per unit area acquisition zone 56 is created relative to the higher average density and higher average basis weight storage zone 58. Additionally, discrete particles of absorbent gelling material are added to an air-entrained stream of fibers prior to their deposition onto the preform to affect uniform distribution of absorbent gelling material throughout the preformed absorbent member 42. Thus, the resultant absorbent member 42 contains a uniform mixture of hydrophilic fibrous material and discrete particles of absorbent gelling material.

In use, the diaper 20 is applied to a wearer, by positioning the back waistband region 24 under the wearer's back, and drawing the remainder of the diaper 20 between the wearer's legs so that the front waistband region 22 is positioned across the front of the wearer. The ends of the tape-tab fasteners 46 are then secured preferably to outwardly facing areas of the diaper 20. In use, disposable diapers or other absorbent articles having such absorbent members 42 having a relatively lower average density and lower average basis weight acquisition zone 56, tends to more quickly acquire liquids into the acquisition zone 56 and to distribute these liquids to the remaining portions of the absorbent member 42 and to remain dry or dryer due to the preferential capillarity between the storage zone and the acquisition zone 56 of the absorbent member 42 and the characteristics of the relatively large particles of absorbent gelling material. Thus, such an absorbent member 42 helps to alleviate leakage around the edges of such absorbent articles.

Figure 5:
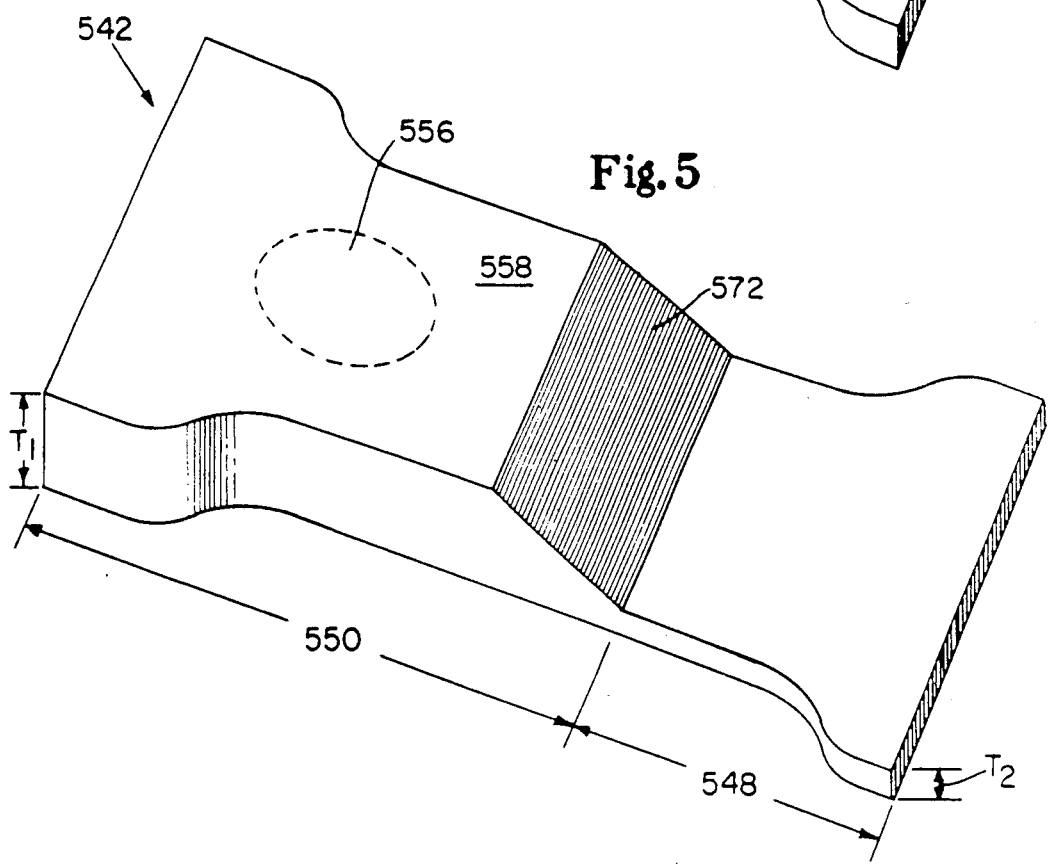
FIG. 5 is a perspective view of an alternative embodiment of the absorbent member of the present invention.

FIG. 5 shows an alternative embodiment of an absorbent member 542 of the present invention. As shown in FIG. 5, the front section 550 of the absorbent member 542 has a thickness, T1, greater than the thickness, T2, of the back section 548. The acquisition zone 56 is preferably of the same thickness, T1, as the storage zone 58 positioned in the front section 550 of the absorbent member 542; the front section 550 having a terraced character by virtue of the thickness difference between the front section 550 and the back section 548 and by virtue of the relatively steep slope formed by a density/basis weight transition zone which is designated 572. Preferably, T1 is at least about 1.5 times as great as T2 and preferably about 2.0 times as great as T2. In this preferred embodiment, about three-fourths of the absorbent material is disposed in the front section 550 of the absorbent member 542 thereby providing an absorbent member 542 wherein the front section 552 has high absorbent capacity as well as rapid acquisition characteristics.

FIGS. 6 and 7 show a further alternative embodiment of an absorbent member 642 the present invention. An absorbent acquisition core 674 is positioned over the absorbent member 642 of the present invention to form a dual-layer absorbent core. An example of a similar dual-layer absorbent core is discussed in more detail in the above-referenced U.S. Pat. No. 4,673,402 of Paul T. Weisman, Dawn I. Houghton, and Dale A. Gellert, which is incorporated herein by reference.

The absorbent acquisition core 674 preferably consists essentially of hydrophilic fibrous material. This absorbent acquisition core 674 thus serves to quickly collect and temporarily hold discharged liquids and to transport such liquids by wicking from the point of initial contact to other parts of the absorbent acquisition core 674. Since the primary function of the absorbent acquisition core 674 is to receive liquids passing through the topsheet 38 and to transport such liquids to other areas of the absorbent acquisition core 674 and eventually onto the absorbent member 642, the absorbent acquisition core 674 can be substantially free of absorbent gelling material. Alternatively, the absorbent acquisition core 674 can contain particular amounts of absorbent gelling material. Thus, the absorbent acquisition core 674, for example, can contain up to about 50%, or preferably up to between about 25% and 40%, by its weight of particles of absorbent gelling material. In the most preferred embodiments, the absorbent acquisition core contains up to about 8% by its weight of particles of absorbent gelling material. In some instances, the presence of particles of absorbent gelling material in the absorbent acquisition core 674 can actually serve to maintain its density within the optimum range to promote fluid distribution. The specific type and particle size distribution of the absorbent gelling material optionally used in the absorbent acquisition core 674 does not have to be the same as that essentially employed in the absorbent member 642, although the same type and particle size distribution are preferred.

The shape, size and character, including capillarity of the absorbent acquisition core 674, is of some importance in determining the effectiveness of the resulting diaper 20 or other absorbent article. The absorbent acquisition core 674 in the unfolded configuration can be of any desired shape, for example, rectangular, oval, oblong, asymmetric or hourglass-shaped. The shape of the absorbent acquisition core 674 will frequently define the general shape of the resulting diaper 20. In preferred embodiments of the present invention as shown in FIG. 6, the absorbent acquisition core 674 will be hourglass-shaped and will be of a substantially uniform density within the range of from about 0.07 to about 0.20 g/cm$^3$. Preferably, the core will have a basis weight ranging from about 0.007 to about 0.075 g/cm$^2$.

The absorbent acquisition core 674 may alternatively comprise one or more core acquisition zones (not shown) having a lower average density and a lower average basis weight than the remainder of the absorbent acquisition core 674. The core acquisition zone or zones may have the same shape, positioning and characteristics as the acquisition zone 656 of the absorbent member 642, or they may have different shapes, positioning and/or characteristics. Preferably, the core acquisition zone of the absorbent acquisition core 674 corresponds in positioning and shape with at least a portion of the acquisition zone 656 of the absorbent member 642, and more preferably the entire acquisition zone 656 of the absorbent member 642, so as to provide an overall acquisition zone extending throughout the entire thickness of the dual-layer absorbent core system.

The absorbent member 642 of the present invention need not be as large as the absorbent acquisition core 674 and can, in fact, have a top surface area which is substantially smaller than the top surface area of the absorbent acquisition core 674. Generally, the absorbent member 674 will have a top surface area from about 0.25 to about 1.0 times that of the absorbent acquisition core 674. Most preferably, the top surface area of the absorbent member 642 will be only from about 0.25 to about 0.75, and most preferably from about 0.3 to about 0.5, times that of the absorbent acquisition core 674.

The absorbent member 642 is preferably placed in a specific positional relationship with respect to the backsheet 40 and/or the absorbent acquisition core 674 in the diaper or other absorbent article. More particularly, the absorbent member 642 is positioned generally toward the front of the diaper so that absorbent gelling material is most effectively located to acquire and hold discharged liquids from the absorbent acquisition core 674.

The forward postioning of the absorbent member 642 can be defined by specifying the percent of total absorbent gelling material which is found forward of particular points along the length of the diaper or other absorbent article. Thus, in accordance with the present invention, the absorbent member 642 is positioned relative to the backsheet and/or the absorbent acquisition core such that (1) at least about 75% of the total absorbent gelling material in the absorbent member 642 is found within the front two-thirds portion of the diaper or other absorbent article, and (2) at least about 55% of the total absorbent gelling material in the absorbent member 642 is found within the front half portion of the diaper or other absorbent article. More preferably, the absorbent member 642 is positioned relative to the backsheet 38 and/or the absorbent acquisition core 674 such that at least about 90% of the total absorbent gelling material in the absorbent member 642 is found in the front two-thirds portion and at least about 60% of the total absorbent gelling material is found in the front half portion of the diaper or other absorbent article. (As noted, for purposes of the present invention, "portions" of the diaper or other absorbent article can be defined by reference to the top surface area of the unfolded diaper 20 or absorbent article found in front of a given point on the line which defines the length of the diaper 20 or absorbent article.)

In the usual instance when the absorbent acquisition core 674 generally defines the shape of the diaper or other absorbent article, the normal length of the backsheet 38 will be approached by the longest longitudinal dimension of the absorbent acquisition core 674. In such instances, the positioning of the absorbent member 642 can also be defined with respect to its location toward the front portion of the absorbent acquisition core 674. However, in some applications (e.g. adult incontinence articles) wherein bulk reduction or minimum cost are important, the absorbent acquisition core would not take on the general shape of the diaper or incontinence structure. Rather it would be generally located to cover only the genital region of the wearer and could in this case have approximately the same top surface area as the absorbent member 642. In this instance, both the absorbent acquisition core 674 and the co-extensive absorbent member 642 would be located toward the front of the article as defined by only the backsheet 38 such that the requisite percentages of absorbent gelling material would be found in the front two-thirds and front half sections respectively of the diaper or other absorbent article.

The absorbent member 642 of the dual-layer absorbent core can be of any desired shape consistent with comfortable fit including, for example, circular, rectangular, trapezoidal, oblong, hourglass-shaped, dog-bone-shaped, or oval. If desired, the absorbent member 642 can be wrapped in a high wet strength envelope web such as tissue paper or a synthetic fine pore, e.g., nonwoven material, to minimize the potential for particles of absorbent gelling material to migrate out of the absorbent member 642. Another objective of such overwrapping is to desirably increase the in-use integrity of the dual layer absorbent core. Such a web can, in fact, be glued to the absorbent member 642. Suitable means for carrying out this gluing operation include the glue spraying procedure described in U.S. Pat. No. 4,573,986 issued to Minetola and Tucker, on Mar. 4, 1986, which patent is incorporated herein by reference.

In preferred embodiments, the absorbent member 642 of the dual layer absorbent core will be oblong. In especially preferred embodiments, an oblong absorbent member 642 overwrapped with spray-glued tissue will be employed.

Because the absorbent member 642 of the dual-layer absorbent core is generally smaller than the absorbent acquisition core 674 such that the absorbent member 642 may entirely be placed in the area of typical liquid deposition, and because the absorbent member 642 is preferably positioned in a specific positional relationship with respect to the backsheet 38 and/or the absorbent acquisition core 674, the acquisition zone 656 may be positioned anywhere in the absorbent member 642. The acquisition zone 656 is not necessarily limited to a portion of the deposition region, since in effect the entire absorbent member 642 of the dual-layer absorbent core is in the "deposition region". The acquisition zone 656 is, however, preferably positioned in a specific positional relationship with respect to the backsheet 38 and/or the absorbent acquisition core 674 of the diaper or other absorbent article. More particularly, the acquisition zone 656 should be positioned generally toward the front of the diaper at least partially in the crotch region 26 so that the acquisition zone 656 is most effectively located to quickly acquire and distribute liquids within the absorbent member 642. Thus, the positioning of the acquisition zone 656 in the diaper or other absorbent article can be defined by specifying the percentage of the top surface area (and/or volume) which is found forward of a particular point along the length of the diaper or other absorbent article. In accordance with the present invention, the acquisition zone 656 is preferably positioned relative to the backsheet 39 and/or the absorbent acquisition core 674 such that the top surface area of the acquisition zone 656 is completely positioned within the front two-thirds portion of the diaper or absorbent article. More preferably, the acquisition zone 656 is positioned relative to the backsheet 38 and/or the absorbent acquisition core 674 such that the top surface area of the acquisition zone 656 is completely positioned within the front half portion of the diaper or absorbent article and, most preferably, such that at least about 30% of the top surface area is located in the front one-third section of the diaper or absorbent article. The acquisition zone 656 is also most preferably completely positioned within the crotch region 26 of the diaper or absorbent article.

In order to maintain a certain minimal absorbency level in the front portions of the diaper or other absorbent article, it has been found that the top surface area of the acquisition zone 656 should comprise less than the entire top surface area of the absorbent member 642 of the dual-layer absorbent core. The top surface area (and/or volume) of the acquisition zone 656 preferably comprises less than about 50% of the top surface area (and/or volume) of the absorbent member 642. More preferably, the top surface area of the acquisition zone 656 comprises less than about 35% of the top surface area of the absorbent member 642 and most preferably less than about 20% of the top surface area of the absorbent member 642. All other aspects of the acquisition zone 656 may be similar to the acquisition zone 56 discussed with respect to the absorbent member 42.

FIG. 8 shows a still further alternative embodiment of an absorbent member 842 of the present invention. The absorbent member 842 has an asymmetric shape (i.e., the absorbent member 842 is not symmetrical about its transverse centerline). In addition, the density and basis weight values of the ear regions 860 and 862 and the back section 848 are different from the storage zone 858 positioned in the central region 864 by virtue of the method by which the absorbent member 842 is formed. The ear regions 860 and 862 and the back section 848 are preferably formed with a lesser basis weight than the storage zone 858 of the central region 864 because the extra material would, in this embodiment, provide no significant incremental benefits in leakage protection such that the cost of such absorbent members 842 is lowered. The absorbent member 842 is calendered to a uniform thickness; the storage zone 858 of the central region 864, therefore, having a greater average density than the back section 848 and the ear regions 860 and 862. (It should be understood that all or portions of the back section 848 and the ear regions 860 and 862 may alternatively be calendered to a lesser thickness than the central region 864 such that they have about an equal or a greater average density than the storage zone 858.) Further, as shown in FIG. 8, the back section 848 preferably does not contain ears, although it alternatively may contain such ears.

The acquisition zone 856 of the absorbent member 842 has a funnel shape. The funnel shape is defined by a generally triangular portion 884 in combination with a stem or rectangular portion 886. The triangular portion 884 is especially effective in absorbing liquids discharged by a male wearer, while the stem portion 886 is effective for a female wearer. In order to resist closure of the stem portion 884 of the acquisition zone 856 during manufacture or use, the stem portion 884 should have a minimum width, preferably at least about ⅜ inch for the fibrous material preferably used herein. The shape of the acquisition zone 856 may also vary according to the type of wearer contemplated, such as preferably only a triangular portion 884 for a male wearer.

Figure 9:
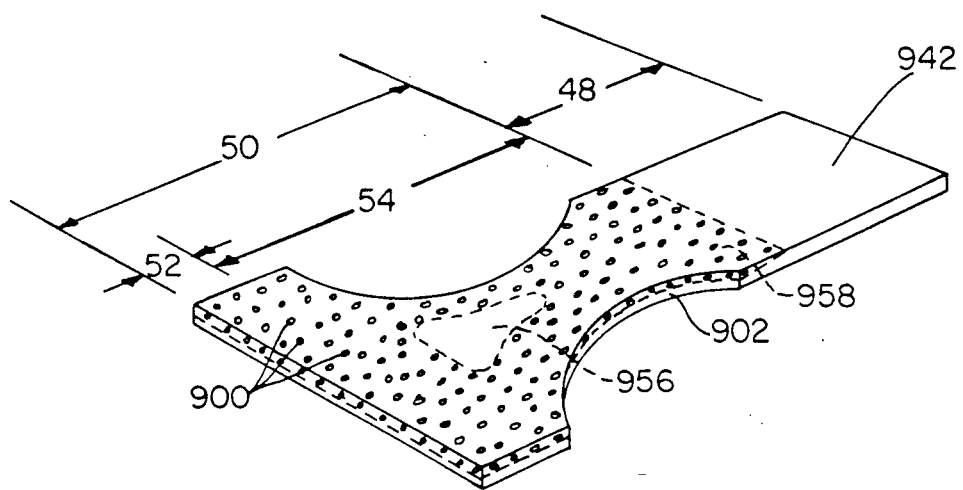
FIG. 9 is a perspective view of another alternative embodiment of the absorbent member of the present invention.

FIG. 9 shows a further alternative embodiment of the present invention in which the absorbent member 942 comprises a stratified matrix of hydrophilic fibrous material and a mixture of hydrophilic fibrous material and relatively large particles 900 of absorbent gelling material. The absorbent member 942 thus comprises a storage zone 958 (designated by the dotted lines), an acquisition zone 956 (designated by the dotted lines), and a dusting layer 902 (acquisition/distribution layer). The storage zone 958 is preferably positioned only in the front section 850 of the absorbent member 942 such that the back section 48 does not comprise a storage zone 958 (i.e., the back section 48 does not comprise a mixture of hydrophilic fibrous material and particles of absorbent gelling material). This configuration both saves on material costs since absorbent gelling material is relatively expensive and provides a leakage benefit at the end of the absorbent member 942. In addition, both the storage zone 958 and the acquisition zone 956 do not comprise the entire thickness of the absorbent member 942, but extend only through a fraction (preferably between about 25% and about 75%) of the total thickness of the absorbent member 942. Thus, the dusting layer 902 is formed from at least the portion of the thickness of the absorbent member 942 not comprising the acquisition zone 956 and the storage zone 958; preferably, the dusting layer 902 also being formed from the back section 48 of the absorbent member 942. In the embodiment illustrated, both the acquisition zone 956 and the dusting layer 902 preferably consist essentially of hydrophilic fibrous material that has limited quantities (0% to about 8% by weight) of absorbent gelling material dispersed therein. Further, the acquisition zone 956 and the dusting layer 902 are made of the same materials and have the same density and basis weight so that the absorbent member 942 has, in essence, an overall acquisition zone surrounding the storage zone 958.

Body liquids that are deposited onto the acquisition zone 956 will be quickly acquired into the absorbent member 942 where they will be either transported into the storage zone 958 by the capillary gradient between the storage zone 958 and the acquisition zone 956 along their interface, or wicked or pulled by gravity into the dusting layer 902 whereupon the liquids will be rapidly transported by wicking from the point of initial contact at the acquisition zone 956 to other parts of the dusting layer 902 where the capillary difference between the dusting layer 902 and the storage zone 958 will cause the liquid to be transported into the storage zone 958. Thus, a greater area of capillary gradients exists between the storage zone 958 and other portions of the absorbent member 942 such that the storage zone 958 and, more particularly, the particles 900 of absorbent gelling material are more efficiently used. Thus, while the acquisition zone 956 and the dusting layer 902 may have different characteristics and constructions such as being made of different materials, having different densities, or having particles of absorbent gelling material dispersed in either, it is preferred that the acquisition zone 956 and the dusting layer 902 consist of the same material, have the same density, and be essentially devoid of particles of absorbent gelling material so that the liquids may rapidly wick into and through the absorbent member 942.

The absorbent member 942 of this alternative embodiment is preferably manufactured by the methods and apparatus disclosed in U.S. patent application Ser. No. 06/868,217 filed May 28, 1986, by John J. Angstadt, which application is incorporated herein by reference. Thus, the absorbent member 942 is preferably made by airlaying a layer of only fibrous material onto a profiled absorbent member-preform to form what will be the dusting layer 902 and the acquisition zone 956. The storage zone 956 is then formed by airlaying a mixture of fibrous material and particles 900 of absorbent gelling material over the dusting layer 902 to form the storage zone 958. The absorbent member 942 is then calendered to a uniform thickness.

Figure 10:
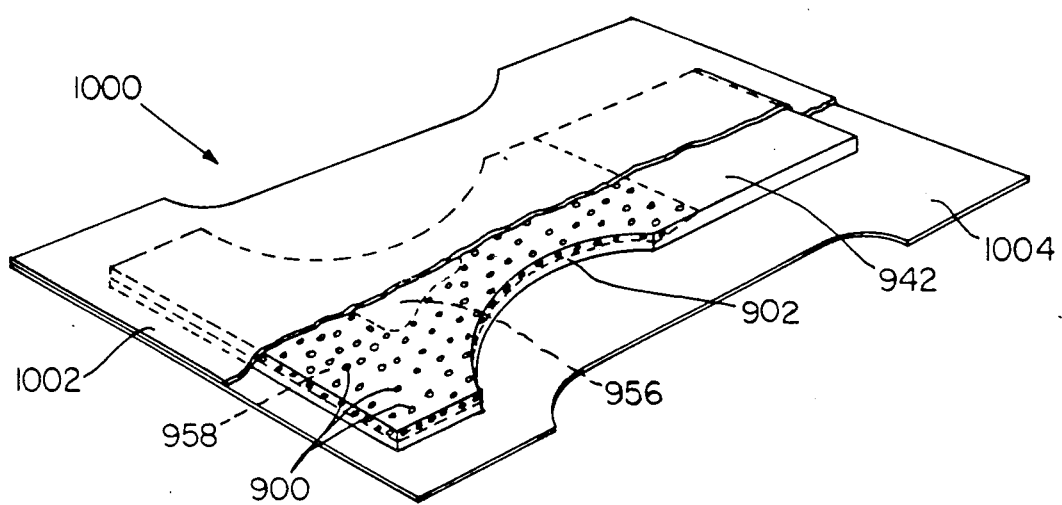
FIG. 10 is a cut-away perspective view of a disposable diaper embodiment of the present invention containing the absorbent member shown in FIG. 9.

FIG. 10 shows a perspective view of an alternative diaper embodiment of the present invention in which the absorbent member 942 of FIG. 9 is encased between a topsheet 1002 and a backsheet 1004 to form the disposable diaper 1000. The absorbent member 942 is preferably positioned such that the dusting layer 902 is positioned adjacent the backsheet 1004 so that the absorbent member 942 may function as hereinbefore described. Although not preferred, the storage zone 958 may alternatively be positioned adjacent the backsheet 1004 so that the dusting layer 902 acts as a fluid distribution/acquisition layer and the storage zone 958 acts as a lower fluid storage layer such as the structure described in the hereinbefore referenced U.S. Pat. No. 4,673,402.

Figure 11:
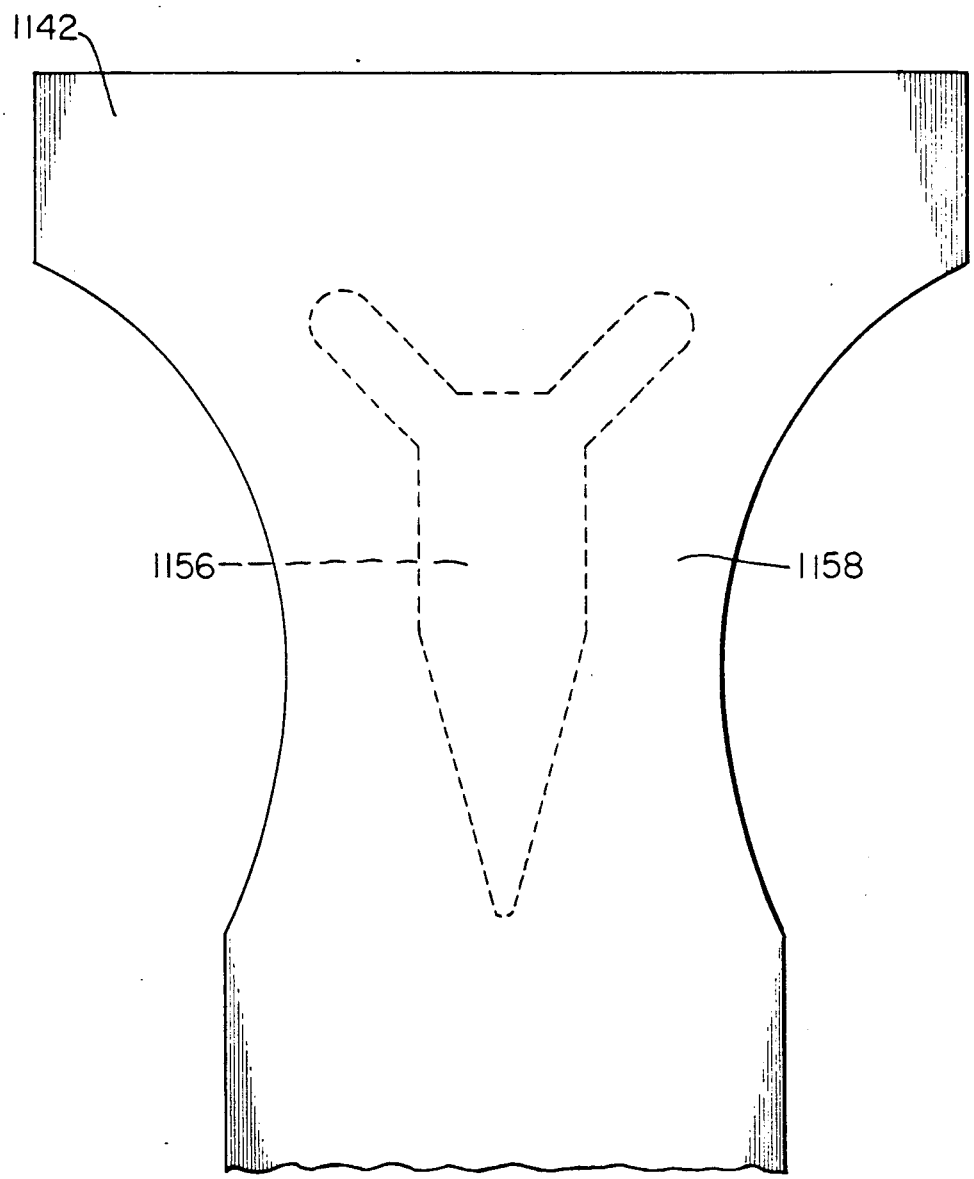
FIG. 11 is a top view of a portion of an absorbent member according to the present invention showing a preferred shape for the acquisition zone.

FIG. 11 shows a further alternative embodiment of the present invention wherein the shape of the acquisition zone 1156 (shown by the dotted lines) is "fox-shaped." (So called because it resembles the front profile of a fox's head.) As previously discussed, a triangular acquisition zone has been found to be especially effective for male wearers. However, such an acquisition zone does not perform as well for female wearers. It has been found that an optimized shape for an acquisition zone for females is the fox-shape shown in FIG. 11. The fox-shape increases the perimeter of the interface between the acquisition zone 1156 and the storage zone 1158. In addition, the fox-shape is positioned farther from the front end of the absorbent member 1142 than the triangular acquisition zone utilized for males so as to be placed nearest the point of discharge because of the anatomical differences between males and females. Thus, the fox-shaped acquisition zone 1156 enhances fluid distribution for female wearers.

Yet another alternative to each of the embodiments of the above absorbent members of the present invention comprises varying the pore size of the fibers without necessarily varying the density of the fibers to form an acquisition zone and a storage zone. For example, fine fiber dimensions of hardwood fluff can be utilized to advantage by substituting at least about 50%, and preferably about 80% to 100%, hardwood fluff fibers of approximately the same density as lower density softwood fluff fibers for the softwood fibers in the storage zone. This can be done because the hardwood fluff has a smaller pore size than the softwood fluff material. As result, a capillarity difference will still be obtained within the scope of the invention, even if the density of each zone is the same. Thus, for example, an absorbent member can be obtained from using a predominately softwood pulp with a fine pore structure to define the acquisition zone and a predominately hardwood fluff pulp to define the storage zone.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent member having a back section and a front section contiguous with said back section, said front section having an end region and a deposition region contiguous with said end region and said back section so that said deposition region is positioned between said end region and said back section, the absorbent member comprising:

a storage zone positioned in at least said deposition region of the absorbent member; and an acquisition zone positioned in at least said deposition region of the absorbent member, said acquisition zone having a lower average density and a lower average basis weight per unit area than said storage zone, said storage zone at least partially laterally surrounding the perimeter of said acquisition zone so as to be in liquid communication with at least a portion of the lateral area of said acquisition zone; and a mixture of hydrophilic fibrous material and discrete particles of absorbent gelling material, said particles of absorbent gelling material having a mass median particle size ranging from about 400 microns to about 1680 microns.

2. The absorbent member of claim 1 wherein said particles of absorbent gelling material have a mass median particle size ranging from about 400 microns to about 1410 microns.

3. The absorbent member of claim 2 wherein no more than about 16% by weight of said particles have a particle size less than 200 microns.

4. The absorbent member of claim 3 wherein no more than about 16% by weight of said particles have a particle size greater than 1410 microns.

5. The absorbent member of claim 1 wherein said particles of absorbent gelling material have a mass median particle size ranging from about 400 microns to about 1190 microns.

6. The absorbent member of claim 5 wherein said particles of absorbent gelling material have a mass median particle size greater than or equal to about 420 microns.

7. The absorbent member of claim 5 wherein said particles of absorbent gelling material have a mass median particle size greater than or equal to about 500 microns.

8. The absorbent member of claims 1, 2, 5, 6, or 7 wherein said acquisition zone is completely positioned within said deposition region, comprises less than about 35% of the top surface area of said front section, and is transversely centered within said deposition region.

9. The absorbent member of claim 1 wherein no more than about 16% by weight of said particles have a particle size less than 200 microns.

10. An absorbent member having a back section and a front section contiguous with said back section, said front section having an end region and a deposition region contiguous with said end region and said back section so that said deposition region is positioned between said end region and said back section, the absorbent member comprising:
- a storage zone positioned in at least said deposition region of the absorbent member;
- an acquisition zone positioned in at least said deposition region of the absorbent member, said acquisition zone having a lower average density and a lower average basis weight per unit area than said storage zone, said storage zone at least partially laterally surrounding the perimeter of said acquisition zone so as to be in liquid communication with at least a portion of the lateral area of said acquisition zone; and
- a mixture of hydrophilic fibrous material and discrete particles of absorbent gelling material, said particles of absorbent gelling material having a mass median particle size ranging from about 841 microns to about 1680 microns.

11. The absorbent member of claim 10 wherein said acquisition zone is completely positioned within said deposition region, comprises less than about 35% of the top surface area of said front section, and is transversely centered within said deposition region.

12. The absorbent member of claim 11 wherein said storage zone and said acquisition zone extend through only a fraction of the total thickness of the absorbent member so as to form a dusting layer.

13. The absorbent member of claim 12 wherein said dusting layer and said acquisition zone have the same density and basis weight, and both said dusting layer and said acquisition zone consist essentially of hydrophilic fibrous material.

14. The absorbent member of claims 10, 11, or 12 wherein between 0% and about 20% by weight of said particles have a particle size less than about 841 microns.

15. The absorbent member of claims 10, 11, or 12 wherein said particles of absorbent gelling material have a mass median particle size ranging from about 841 microns to about 1410 microns.

16. The absorbent member of claims 10, 11, or 12 wherein said particles of absorbent gelling material have a mass median particle size ranging from about 841 microns to about 1190 microns.

17. The absorbent member of claim 16 wherein between 0% and about 20% by weight of said particles have a particle size less than about 841 microns, and no more than about 16% by weight of said particles have a particle size greater than about 1190 microns.

18. The absorbent member of claim 11 wherein the top surface area of said acquisition zone has a triangular shape.

19. The absorbent member of claim 11 wherein the top surface of said acquisition zone is fox-shaped.

20. An absorbent article comprising:
- a liquid pervious topsheet;
- a liquid impervious backsheet associated with said topsheet; and
- an absorbent member according to claims 1, 3, 10, or 14 positioned between said topsheet and said backsheet.

21. An absorbent article having a front waistband region, a back waistband region and a crotch region, said absorbent article comprising:
- a liquid pervious topsheet;
- a liquid impervious backsheet associated with said topsheet; and
- an absorbent member positioned between said topsheet and said backsheet, said absorbent member comprising a storage zone and an acquisition zone having a lower average density and a lower average basis weight per unit area than said storage zone, said acquisition zone being positioned with respect to the absorbent article such that the top surface area of said acquisition zone is at least partially positioned in said crotch region, said absorbent member comprising a mixture of hydrophilic fibrous material and discrete particles of absorbent gelling material, said particles of absorbent gelling material having a mass median particle size ranging from about 400 microns to about 1190 microns.

22. The absorbent article of claim 21 additionally comprising an absorbent acquisition core positioned between said topsheet and said absorbent member.

23. The absorbent article of claim 22 wherein said absorbent member is generally oblong and has a top surface area that is from about 0.25 to about 1.0 times that of said absorbent acquisition core, said absorbent member being positioned relative to said backsheet and said absorbent acquisition core in a manner such that at least 75% of the absorbent gelling material in said absorbent member is found within the front two-thirds portion of the absorbent article.

24. The absorbent article of claim 21 wherein said particles of absorbent gelling material have a mass median particle size greater than or equal to about 420 microns.

25. The absorbent article of claim 21 wherein said particles of absorbent gelling material have a mass median particle size greater than or equal to about 500 microns.

26. The absorbent article of claims 24 or 25 wherein no more than about 16% by weight of said particles have a particle size less than 210 microns, and no more than about 16% by weight of said particles have a particle size greater than about 1190 microns.

* * * * *